US012629322B2

(12) United States Patent
Jim et al.

(10) Patent No.: US 12,629,322 B2
(45) Date of Patent: *May 19, 2026

(54) ANTISEPTIC COMPOSITIONS

(71) Applicant: RHT LIMITED, Hong Kong (CN)

(72) Inventors: Ka Wai Jim, Hong Kong (CN); Rudy Chi Keung Chan, Hong Kong (CN)

(73) Assignee: RHT LIMITED, Hong Kong (CN)

( * ) Notice: Subject to any disclaimer, the term of this patent is extended or adjusted under 35 U.S.C. 154(b) by 258 days.

This patent is subject to a terminal disclaimer.

(21) Appl. No.: 18/002,859

(22) PCT Filed: Jun. 21, 2021

(86) PCT No.: PCT/CN2021/101313
§ 371 (c)(1),
(2) Date: Dec. 21, 2022

(87) PCT Pub. No.: WO2021/259211
PCT Pub. Date: Dec. 30, 2021

(65) Prior Publication Data

US 2023/0301884 A1      Sep. 28, 2023

Related U.S. Application Data

(60) Provisional application No. 63/042,015, filed on Jun. 22, 2020.

(51) Int. Cl.
A61K 8/34          (2006.01)
A61K 8/36          (2006.01)
(Continued)

(52) U.S. Cl.
CPC .............. A61K 8/345 (2013.01); A61K 8/347 (2013.01); A61K 8/361 (2013.01); A61K 8/37 (2013.01);
(Continued)

(58) Field of Classification Search
USPC .......................................................... 424/401
See application file for complete search history.

(56) References Cited

U.S. PATENT DOCUMENTS

| | | |
|---|---|---|
| 5,891,428 A | 4/1999 | Greff |
| 9,750,755 B2 | 9/2017 | Ahmed et al. |

(Continued)

FOREIGN PATENT DOCUMENTS

| | | |
|---|---|---|
| CN | 1195284 A | 10/1998 |
| CN | 1620248 A | 5/2005 |

(Continued)

OTHER PUBLICATIONS

"Skin cancer treatments", American cancer society, 2024 (Year: 2024).*

(Continued)

*Primary Examiner* — Kyung S Chang
(74) *Attorney, Agent, or Firm* — EAGLE IP LIMITED

(57) ABSTRACT

In one aspect, provided is an aqueous antiseptic composition comprising glycerin 8.5-16% by weight; caprylyl glycol 0.45-3% by weight; and a first ingredient; wherein the first ingredient is acrylates/C10-30 about 0.01-0.1% by weight or ethoxydiglycol about 1-5% by weight. The glycerin, the caprylyl glycol and the first ingredient taken together form a first component. A sum of the first component is more than 13% by weight of the antiseptic composition. Other exemplary embodiments are also described. In certain embodiments, provided is an antiseptic composition useful for making skin or hand sanitizers that has a long-lasting, great antiseptic efficacy but at the same time having skin-moisturizing, low toxicity and low skin-irritating, hypo-allergenic properties, low inflammability, and low production cost.

14 Claims, 4 Drawing Sheets

(51) Int. Cl.

| | |
|---|---|
| *A61K 8/37* | (2006.01) |
| *A61K 8/67* | (2006.01) |
| *A61K 8/81* | (2006.01) |
| *A61K 31/047* | (2006.01) |
| *A61K 31/085* | (2006.01) |
| *A61K 31/164* | (2006.01) |
| *A61K 31/19* | (2006.01) |
| *A61K 31/20* | (2006.01) |
| *A61K 31/78* | (2006.01) |
| *A61P 31/00* | (2006.01) |
| *A61P 31/14* | (2006.01) |
| *A61Q 17/00* | (2006.01) |

(52) U.S. Cl.

CPC ............ *A61K 8/673* (2013.01); *A61K 8/8152* (2013.01); *A61K 31/047* (2013.01); *A61K 31/085* (2013.01); *A61K 31/164* (2013.01); *A61K 31/20* (2013.01); *A61K 31/78* (2013.01); *A61P 31/14* (2018.01); *A61Q 17/005* (2013.01); *A61K 2800/30* (2013.01)

(56) References Cited

U.S. PATENT DOCUMENTS

| | | | |
|---|---|---|---|
| 10,959,975 B1 | 3/2021 | Cioe | |
| 2014/0044667 A1 | 2/2014 | Greff | |
| 2017/0347646 A1* | 12/2017 | Macinga | A61K 8/345 |
| 2019/0160033 A1 | 5/2019 | Lim et al. | |
| 2022/0168198 A1* | 6/2022 | Meyer | A61K 8/35 |

FOREIGN PATENT DOCUMENTS

| | | | |
|---|---|---|---|
| CN | 102803460 A | 11/2012 | |
| CN | 107308018 A | 11/2017 | |
| CN | 108567581 A | 9/2018 | |
| CN | 110494190 A | 11/2019 | |
| EP | 1818060 A1 | 8/2007 | |
| EP | 0996418 B2 * | 4/2009 | A61P 17/06 |
| WO | 9747310 A1 | 12/1997 | |
| WO | WO-2020147953 A1 * | 7/2020 | A01N 31/08 |

OTHER PUBLICATIONS

"Tolnaftate (Topical Route)", Mayo Clinic, Feb. 1, 2024, retrieved from internet <URL: https://www.mayoclinic.org/drugs-supplements/tolnaftate-topical-route/description/drg-20068886?p=1>, [retrieved on Jul. 26, 2024].

"What Is The Difference Between Antiseptic And Antibiotic", Safetec, May 24, 17, retrieved from internet <URL: https://safetec.com/blog/first-aid/what-is-the-difference-between-antiseptic-and-antibiotic/>, [retrieved on Jul. 26, 2024].

"Cosmetic raw material: 1,2 Hexanediol", ChemKnock, Jul. 26, 2024, retrieved from internet <URL: <www.https://chemknock.com/view.do?no=194&pgMode=view&dvsn=pdt&idx=37341>, [retrieved on Jul. 26, 2024].

* cited by examiner

ANTISEPTIC COMPOSITIONS

FIELD OF INVENTION

This invention relates to the field of antiseptic preparations. More specifically, the present invention relates to antiseptic compositions useful for making skin or hand sanitizers.

BACKGROUND OF INVENTION

Antiseptic agents used for making hand or skin sanitizers play an important role in current personal hygiene and public health. Alcohol (such as ethanol or isopropanol) based compounds comprise a class of proven surface sanitizers and disinfectants that have been commonly used worldwide, but their disadvantages of high inflammability, toxicity, skin dryness, chapping and irritation caused by repeated or prolonged use and temporal disinfecting effect etc. are also well known. An improved antiseptic composition is highly desired.

SUMMARY OF INVENTION

In the light of the foregoing background, in certain embodiments, it is an object to provide an alternate antiseptic composition to overcome at least one of the disadvantages of the prior art.

Accordingly, in certain embodiments, one aspect provides an aqueous antiseptic composition. The composition includes an aqueous mixture of a first component comprising: glycerin about 8.5-16% by weight; caprylyl glycol about 0.45-3% by weight and a first ingredient; wherein the first ingredient is acrylates/C10-30 about 0.01-0.1% by weight or ethoxydiglycol about 1-5% by weight. The glycerin, the caprylyl glycol, and the first ingredient taken together form a first component. A sum of the first component is more than 13% by weight of the antiseptic composition.

In certain exemplary embodiments, the composition is non-alcoholic, that is, free of or essentially free of simple alcohols such as ethanol, isopropanol (isopropyl alcohol) or n-propanol. In certain exemplary embodiments, the effective antiseptic ingredients in the composition comprise glycerin, caprylyl glycol, acrylates/C10-30 or ethoxydiglycol and combinations thereof. In certain exemplary embodiments, the composition is water based. In certain exemplary embodiments, the composition is useful for making skin or hand rubs, washes or sanitizers. In certain exemplary embodiments, the composition can be used as disinfectants and is useful for making surface coatings for disinfecting objects.

Now, it has been surprisingly found that at least some of the problems of the prior art can be overcome by an antiseptic composition described in certain exemplary embodiments that includes: glycerin about 8.5-16% by weight and caprylyl glycol about 0.45-3% by weight. In a further exemplary embodiment, a sum of the glycerin and the caprylyl glycol is more than 13% by weight of the antiseptic composition. In a further exemplary embodiment, the composition further comprises ethoxydiglycol about 1-5% by weight. In yet another exemplary embodiment, the composition further comprises acrylates/C10-30 about 0.01-0.1% by weight.

Other exemplary embodiments will be described herein.

According to another aspect, provided is a skin or hand sanitizer comprising the antiseptic compositions described herein.

According to another aspect, provided is an antiseptic surface coating comprising the antiseptic compositions described herein.

In a further aspect, provided is a method of making the antiseptic composition.

In a further aspect, provided is a use of an antiseptic composition, wherein the composition comprises glycerin about 8.5-16% by weight; caprylyl glycol about 0.45-3% by weight; ethoxydiglycol about 1-5% by weight; and water.

There are many advantages to the present invention. In certain embodiments, provided is a non-alcoholic based antiseptic composition that has a long-lasting, antiseptic efficacy and low inflammability. In certain embodiments, provided is an antiseptic composition having skin-moisturizing, low toxicity and low skin-irritating, hypo-allergenic properties. In certain embodiments, provided is an antiseptic composition having a low production cost. In certain embodiments, the antiseptic compositions provide good antimicrobial (including but not limited to, antibacterial, antifungal and antiviral) efficacy and short action time (say, effective to kill microorganisms within a short period of time, such as 30 seconds or 60 seconds). In certain embodiments, there is no need to add additional preservatives because the compositions are self-preservatives. In certain embodiments, the composition forms an antiseptic invisible film or "glove" on the skin or hands, such that it provides long term antiseptic protection.

DETAILED DESCRIPTION OF THE PREFERRED EMBODIMENTS

Figure 1B:
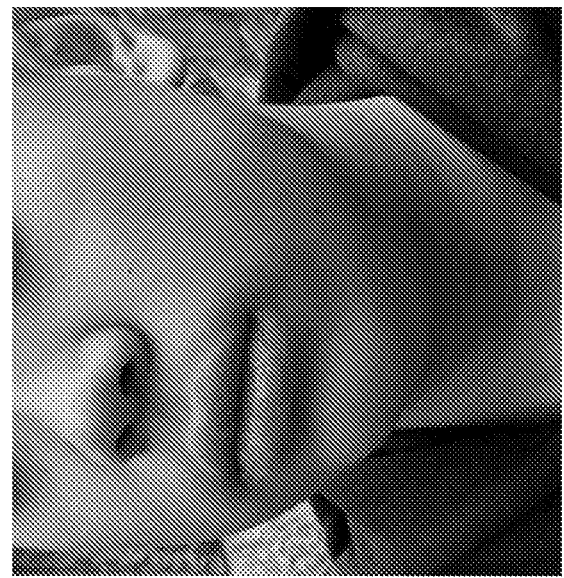
FIG. 1B is a picture showing the same patient's face after use of exemplary Composition, according to the same example embodiment of FIG. 1A.

As used herein and in the claims, "comprising" means including the following elements but not excluding others. The terms "comprising" (or any related form such as "comprise" and "comprises"), "including" (or any related forms such as "include" or "includes"), "containing" (or any related forms such as "contain" or "contains"), means including the following elements but not excluding others. It shall be understood that for every embodiment in which the term "comprising" (or any related form such as "comprise" and "comprises"), "including" (or any related forms such as "include" or "includes"), or "containing" (or any related forms such as "contain" or "contains") are used, this disclosure/application also includes alternate embodiments where the term "comprising", "including," or "containing," is replaced with "consisting essentially of" or "consisting of". These alternate embodiments that use "consisting of" or "consisting essentially of" are understood to be narrower embodiments of the "comprising", "including," or "containing," embodiments.

For example, alternate embodiments of "a composition comprising A, B, and C" would be "a composition consisting of A, B, and C" and "a composition consisting essentially of A, B, and C." Even if the latter two embodiments are not explicitly written out, this disclosure/application includes those embodiments. Furthermore, it shall be understood that the scopes of the three embodiments listed above are different.

As used in the specification and the claims, the singular forms of "a" and "an" also include the corresponding plurals unless the context clearly dictates otherwise. Thus, e.g. the term "a polyol" may also refer to "a plurality of polyols".

As used in the specification and the claims, the term "percentage by weight" or "% by weight" means the percentage (%) by weight of a component relative to the total weight of the entire composition.

The terms "about", "substantially" and "approximately" in the context of the specification denotes an interval of accuracy that a person skilled in the art will understand to still ensure the technical effect of the feature in question. The term typically indicates a deviation from the indicated numerical value of 10% and preferably 5%. For example, having a weight percent of about 20% is the same as a weight percent of 18%-22% or 19% to 21%.

As used herein and in the claims, "disinfectants" refers to agents or chemicals that apply to non-living objects to destroy microorganisms.

As used herein and in the claims, "antiseptics" or "antiseptic agents" refers to agents or chemicals that apply to living tissue or skin to reduce the possibility of infection caused by the microorganisms thereon. The microorganisms may be, but are not limited to, bacteria, viruses, fungi such as yeasts or mould.

As used herein and in the claims, "sanitizer" refers to liquid, gel, or foam generally used to decrease infectious agents, such as microorganisms, on the skin or hands.

As used herein and in the claims, "simple alcohol" refers to one or more short chain volatile or $C_1$-$C_4$ alcohols such as, for example, ethanol, isopropanol (IPA), n-propanol, butanol, isobutanol or a combination thereof, and more particularly ethanol, isopropanol or a combination thereof, and especially ethanol.

As used herein and in the claims, "effective amount" refers to an amount, which is effective at the concentrations used to inactivate or at least substantially reduce the counts of microorganisms such as, for example, bacteria, viruses and/or fungi.

As used herein and in the claims, "biocidal" refers to destroying, rendering harmless, or exerting a controlling effect on any harmful microorganisms.

As used herein and in the claims, "polyol" refers to at least one diol or triol containing 3 to 8 carbon atoms (for example propylene glycol, 1,3-butylene glycol, 1,2-pentanediol, 1,2-octanediol (INCI name caprylyl glycol), 1,8-octanediol, 2-ethyl-1,3-hexanediol, glycerine (1,2,3-propanetriol), mannitol, sorbitol or mixtures thereof). In certain embodiments, the polyol is a glycerine and caprylyl glycol.

As used herein and in the claims, "glycol" refers to at least one monoether of diethyleneglycol or triethyleneglycol or may be a polyalkyleneglycol, for example, methoxydiglycol, ethoxydiglycol, propoxydiglycol, butoxydiglycol and triethyleneglycol monopropyl ether. In certain embodiments, glycol is ethoxydiglycol.

As used herein and in the claims, an "alkyl glycerine and/or the alkyl ester thereof" refers to $R_4OCH_2CH(OH)CH_2OR_5$ wherein $R_4$ is a straight or branched chain alkyl group and $R_5$ is H, a straight or branched chain alkyl group, or a straight or branched alkanoyl group. In some embodiments, $R_4$ contains 6 to 24 carbon atoms and $R_5$ is H or contains 8 to 24 carbon atoms. In some embodiments, $R_4$ is a straight or branched chain alkyl group and $R_5$ is a straight or branched alkanoyl group. The term "glycerine", "glycerin", and "glycerol" are interchangeable.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

For the sake of clarity, if a composition is described as "containing", "contain" or "contains" a particular component, it means that the composition comprises the component but may include other components.

As used herein and in the claims, "aromatic alcohol" refers to compounds comprising a hydroxyl group bonded to a carbon atom which is part of a side chain of an aromatic ring. Examples of aromatic alcohols include but are not limited to as phenoxyethanol, benzyl alcohol and phenethyl alcohol. In some embodiments, the aromatic alcohol is an aromatic alcohol commonly used in dermatological and/or cosmetic compositions.

As used herein and in the claims, "panthenol" refers to an alcohol analog of pantothenic acid (vitamin $B_5$), and is thus a provitamin of $B_5$ with a chemical formula of $C_9H_{19}NO_4$ and with IUPAC name 2,4-Dihydroxy-N-(3-hydroxypropyl)-3,3-dimethylbutanamide. In certain exemplary embodiments, panthenol comes either in D form, or as a mixture of D and L (DL-panthenol).

As used herein and in the claims, "acrylates/C10-30" refers to acrylates/C10-30 alkyl acrylate crosspolymer, which is comprised of a mixture of acrylic acid and methacrylic acid.

As used herein and in the claims, "sanitize" or "sanitizing" refers to the act of rendering a harmful agent inactive, either by killing it or disabling its harmful properties. Harmful agents include, but are not limited to, germs or infective agents such as bacteria, viruses, and fungi. In some embodiments, the act of sanitizing reduces or prevents the spread of disease.

The compositions of the present invention can be used for sanitizing hands, skin, mouth cavity, lips, mucosae, and skin appendages and/or disinfecting surfaces, such as food contact surfaces (e.g., cutting board, cutlery, dining ware), instruments, and food, such as fruit, fruit skin, and vegetables.

In certain exemplary embodiments, the composition is useful for making skin or hand rubs, washes or sanitizers. In certain exemplary embodiments, the composition is useful for making surface coatings for disinfecting objects or preventing the objects from being infected or exposed to infective agents. In certain exemplary embodiments, the composition is antibacterial. In certain exemplary embodiments, the composition is antiviral. In certain exemplary embodiments, the composition is antifungal.

In certain exemplary embodiments, the composition is non-alcoholic, that is, free of or essentially free of alcohols such as ethanol or isopropanol (isopropyl alcohol). In certain exemplary embodiments, the composition comprises a first component selected from glycerin, caprylyl glycol, ethoxydiglycol and combinations thereof. In one exemplary embodiment, the first component in the composition consists essentially of glycerin, caprylyl glycol and ethoxydiglycol. In some embodiments, the composition comprises first components and water. In other embodiments, the composition consists essentially of first components and water.

In certain embodiments, the composition may further comprise one or more compounds. In some embodiments, the composition may further comprise one or more compounds selected from the group consisting of panthenol, sodium polyacrylate, phenoxyethanol, ethylhexyl stearate, Trideceth-6 and ethylhexylglycerin and combinations thereof. In one exemplary embodiment, the panthenol is 0.1% to 1% by weight; the sodium polyacrylate is 0.1% to 0.5% by weight; the phenoxyethanol is 0 to 1% by weight; the ethylhexyl stearate is 0 to 1% by weight; the Trideceth-6 is 0 to 1% by weight; the ethylhexylglycerin is 0 to 2% by weight, based on the antiseptic composition.

In one exemplary embodiment, the composition is free of or essentially free of panthenol. In one exemplary embodiment, the composition is free of or essentially free of polyacrylate. In one exemplary embodiment, the composition is free of or essentially free of phenoxyethanol. In one exemplary embodiment, the composition is free of or essentially free of ethylhexyl stearate. In one exemplary embodiment, the composition is free of or essentially free of Trideceth-6. In one exemplary embodiment, the composition is free of or essentially free of ethylhexylglycerin.

In certain exemplary embodiments, the composition may comprise water which may optimize antimicrobial efficacy and/or moisturizing effect. In certain exemplary embodiments, the composition is in the form of an aqueous composition and comprises aqua (water) from 75 to 90%. In other exemplary embodiments, the composition is in the form of an aqueous composition and comprises aqua (water) from 10 to 90% by weight, 20 to 90% by weight, 30 to 90% by weight, 40 to 90% by weight, 50 to 90% by weight, 60 to 90% by weight, 70 to 90% by weight, 75 to 90% by weight, 80 to 90% by weight, 85 to 90% by weight, based on the entire composition.

In certain exemplary embodiments, the concentrations of glycerin in the compositions of the present invention can include, but are not limited to, for example, concentrations in ranges of from about 5 wt % to about 20 wt %, e.g., from about 8 wt % to about 16 wt %. In other exemplary embodiments, the concentrations of glycerin in the compositions include, but are not limited to, for example, concentrations in ranges of from about 5 wt % to about 70 wt %, from about 5 wt % to about 65 wt %, from about 5 wt % to about 60 wt %, from about 5 wt % to about 55 wt %, from about 5 wt % to about 50 wt %, from about 5 wt % to about 45 wt %, from about 5 wt % to about 40 wt %, from about 5 wt % to about 35 wt %, from about 5 wt % to about 30 wt %, from about 5 wt % to about 25 wt %, from about 5 wt % to about 20 wt %, from about 5 wt % to about 15 wt %, from about 5 wt % to about 10 wt %, from about 8 wt % to about 70 wt %, from about 8 wt % to about 65 wt %, from about 8 wt % to about 60 wt %, from about 8 wt % to about 65 wt %, from about 8 wt % to about 60 wt %, from about 8 wt % to about 55 wt %, from about 8 wt % to about 50 wt %, from about 8 wt % to about 45 wt %, from about 8 wt % to about 40 wt %, from about 8 wt % to about 35 wt %, from about 8 wt % to about 30 wt %, from about 8 wt % to about 25 wt %, from about 8 wt % to about 20 wt %, from about 8 wt % to about 15 wt %, from about 8 wt % to about 10 wt %, from about 10 wt % to about 70 wt %, from about 10 wt % to about 65 wt %, from about 10 wt % to about 60 wt %, from about 10 wt % to about 55 wt %, from about 10 wt % to about 50 wt %, from about 10 wt % to about 45 wt %, from about 10 wt % to about 40 wt %, from about 10 wt % to about 35 wt %, from about 10 wt % to about 30 wt %, from about 10 wt % to about 25 wt %, from about 10 wt % to about 20 wt %, from about 10 wt % to about 15 wt %, from about 12 wt % to about 70 wt %, from about 12 wt % to about 65 wt %, from about 12 wt % to about 60 wt %, from about 12 wt % to about 55 wt %, from about 12 wt % to about 50 wt %, from about 12 wt % to about 45 wt %, from about 12 wt % to about 40 wt %, from about 12 wt % to about 35 wt %, from about 12 wt % to about 30 wt %, from about 12 wt % to about 25 wt %, from about 12 wt % to about 20 wt %, from about 12 wt % to about 15 wt %, from about 14 wt % to about 70 wt %, from about 14 wt % to about 65 wt %, from about 14 wt % to about 60 wt %, from about 14 wt % to about 55 wt %, from about 14 wt % to about 50 wt %, from about 14 wt % to about 45 wt %, from about 14 wt % to about 40 wt %, from about 14 wt % to about 35 wt %, from about 14 wt % to about 30 wt %, from about 14 wt % to about 25 wt %, from about 14 wt % to about 20 wt %, from about 14 wt % to about 15 wt %, from about 16 wt % to about 70 wt %, from about 16 wt % to about 65 wt %, from about 16 wt % to about 60 wt %, from about 14 wt % to about 55 wt %, from about 16 wt % to about 50 wt %, from about 16 wt % to about 45 wt %, from about 16 wt % to about 40 wt %, from about 16 wt % to about 35 wt %, from about 16 wt % to about 30 wt %, from about 16 wt % to about 25 wt %, from about 16 wt % to about 20 wt %, based on the entire composition.

In certain exemplary embodiments, the concentrations of caprylyl glycol in the compositions of the present invention can include, but are not limited to, for example, concentrations in ranges of from about 0.4 wt % to about 3 wt %, e.g., from about 0.45 wt % to about 3 wt %. In other exemplary embodiments, the concentrations of caprylyl glycol in the compositions include, but are not limited to, for example, concentrations in ranges of from about 0.4 wt % to about 20 wt %, from about 0.4 wt % to about 15 wt %, from about 0.4 wt % to about 10 wt %, from about 0.4 wt % to about 5 wt %, from about 0.4 wt % to about 3 wt %, from about 0.4 wt % to about 2 wt %, from about 0.4 wt % to about 1 wt %, from about 0.4 wt % to about 0.8 wt %, from about 0.4 wt % to about 0.6 wt %, from about 0.5 wt % to about 20 wt %, from about 0.5 wt % to about 15 wt %, from about 0.5 wt % to about 10 wt %, from about 0.5 wt % to about 5 wt %, from about 0.5 wt % to about 3 wt %, from about 0.5 wt % to about 2 wt %, from about 0.5 wt % to about 1 wt %, from about 0.5 wt % to about 0.8 wt %, from about 0.5 wt % to about 0.6 wt %, from about 0.6 wt % to about 20 wt %, from about 0.6 wt % to about 15 wt %, from about 0.6 wt % to about 10 wt %, from about 0.6 wt % to about 5 wt %, from about 0.6 wt % to about 3 wt %, from about 0.6 wt % to about 2 wt %, from about 0.6 wt % to about 1 wt %, from about 0.6 wt % to about 0.8 wt %, from about 0.8 wt % to about 20 wt %, from about 0.8 wt % to about 15 wt %, from about 0.8 wt % to about 10 wt %, from about 0.8 wt % to about 5 wt %, from about 0.8 wt % to about 3 wt %, from about 0.8 wt % to about 2 wt %, from about 0.8 wt % to about 1 wt %, from about 1 wt % to about 20 wt %, from about 1 wt % to about 15 wt %, from about 1 wt % to about 10 wt %, from about 1 wt % to about 5 wt %, from about 1 wt % to about 3 wt %, from about 1 wt % to about 2 wt %, from about 1 wt % to about 1.5 wt %, from about 1.2 wt % to about 20 wt %, from about 1.2 wt % to about 15 wt %, from about 1.2 wt % to about 10 wt %, from about 1.2 wt % to about 5 wt %, from about 1.2 wt % to about 3 wt %, from about 1.2 wt % to about 2 wt %, from about 1.2 wt % to about 1 wt %, from about 1.2 wt % to about 0.8 wt %, from about 1.2 wt % to about 1.0 wt %, from about 1.4 wt % to about 20 wt %, from about 1.4 wt % to about 15 wt %, from about 1.4 wt % to about 10 wt %, from about 1.4 wt % to about 5 wt %, from about 1.4 wt % to about 3 wt %, from about 1.4 wt % to about 2 wt %, from about 1.4 wt % to about 1.8 wt %, from about 1.4 wt % to about 1.6 wt %, from about 1.6 wt % to about 20 wt %, from about 1.6 wt % to about 15 wt %, from about 1.6 wt % to about 10 wt %, from about 1.6 wt % to about 5 wt %, from about 1.6 wt % to about 3 wt %, from about 1.6 wt % to about 2 wt %, from about 1.6 wt % to about 1.8 wt %, from about 1.8 wt % to about 20 wt %, from about 1.8 wt % to about 15 wt %, from about 1.8 wt % to about 10 wt %, from about 1.8 wt % to about 5 wt %, from about 1.8 wt % to about 3 wt %, from about 1.8 wt % to about 2 wt %, from about 2 wt % to about 20 wt %, from about 2 wt % to about 15 wt %, from about 2 wt % to about 10 wt %, from about 2 wt % to about 5 wt %, from about 2 wt % to about 3 wt % from about 2 wt % to about 2.5 wt %, from about 2.2 wt % to about 20 wt %, from about 2.2 wt % to about 15 wt %, from about 2.2 wt % to about 10 wt %, from about 2.2 wt % to about 5 wt %, from about 2.2 wt % to about 3 wt %, %, from about 2.4 wt % to about 20 wt %, from about 2.4 wt % to about 15 wt %, from about 2.4 wt % to about 10 wt %, from about 2.4 wt % to about 5 wt %, from about 2.4 wt % to about 3 wt %, from about 2.4 wt % to about 2.5 wt %, from about 2.6 wt % to about 20 wt %, from about 2.6 wt % to about 15 wt %, from about 2.6 wt % to about 10 wt %, from about 2.6 wt % to about 5 wt %, from about 2.6 wt % to about 3 wt %, from about 2.6 wt % to about 2.8 wt %, from from about 2.8 wt % to about 20 wt %, from about 2.8 wt % to about 15 wt %, from about 2.8 wt % to about 10 wt %, from about 2.8 wt % to about 5 wt %, from about 2.8 wt % to about 3 wt %, from about 3 wt % to about 20 wt %, from about 3 wt % to about 15 wt %, from about 3 wt % to about 10 wt %, from about 3 wt % to about 5 wt %, from about 3 wt % to about 4 wt %, from about 3 wt % to about 3.5 wt %, from about 3 wt % to about 3.4 wt %, from about 3 wt % to about 3.3 wt %, from about 3 wt % to about 3.2 wt %, based on the entire composition.

In certain exemplary embodiments, the concentrations of ethoxydiglycol in the compositions of the present invention can include, but are not limited to, for example, concentrations in ranges of from about 1 wt % to about 5 wt %, e.g., from about 2 wt % to about 4 wt %. In other exemplary embodiments, the concentrations of ethoxydiglycol in the compositions include, but are not limited to, for example, concentrations in ranges of from about from about 1 wt % to about 20 wt %, from about 1 wt % to about 15 wt %, from about 1 wt % to about 10 wt %, from about 1 wt % to about 5 wt %, from about 1 wt % to about 3 wt %, from about 1 wt % to about 2 wt %, from about 1 wt % to about 1.8 wt %, from about 1 wt % to about 1.6 wt %, from about 1 wt % to about 1.4 wt %, from about 1 wt % to about 1.2 wt %, 2 wt % to about 20 wt %, from about 2 wt % to about 15 wt %, from about 2 wt % to about 10 wt %, from about 2 wt % to about 5 wt %, from about 2 wt % to about 3 wt %, from about 2 wt % to about 2.8 wt %, from about 2 wt % to about 2.6 wt %, from about 2 wt % to about 2.4 wt %, from about 2 wt % to about 2.2 wt %, from about 3 wt % to about 20 wt %, from about 3 wt % to about 15 wt %, from about 3 wt % to about 10 wt %, from about 3 wt % to about 5 wt %, from about 3 wt % to about 4 wt %, from about 3 wt % to about 3.8 wt %, from about 3 wt % to about 3.6 wt %, from about 3 wt % to about 3.4 wt %, from about 3 wt % to about 3.2 wt %, from about 4 wt % to about 20 wt %, from about 4 wt % to about 15 wt %, from about 4 wt % to about 10 wt %, from about 4 wt % to about 5 wt %, from about 4 wt % to about 4.8 wt %, from about 4 wt % to about 4.6 wt %, from about 4 wt % to about 4.4 wt %, from about 4 wt % to about 4.2 wt %, from about 5 wt % to about 20 wt %, from about 5 wt % to about 15 wt %, from about 5 wt % to about 10 wt %, from about 5 wt % to about 8 wt %, from about 5 wt % to about 7 wt %, from about 5 wt % to about 6 wt %, from about 5 wt % to about 5.8 wt %, from about 5 wt % to about 5.6 wt %, from about 5 wt % to about 5.4 wt %, from about 5 wt % to about 5.2 wt %, based on the entire composition. In certain exemplary embodiments, the composition does not comprise ethoxydiglycol.

In certain exemplary embodiments, the concentrations of sodium polyacrylate in the compositions of the present invention can include, but are not limited to, for example, concentrations in ranges of from about 0.1 wt % to about 0.5 wt %, e.g., about 0.1 wt %, 0.2 wt %, 0.3 wt %, 0.4 wt %, 0.5 wt %. In certain exemplary embodiments, the composition does not comprise sodium polyacrylate.

In certain exemplary embodiments, the concentrations of ethylhexyglycerin in the compositions of the present invention can include, but are not limited to, for example, concentrations in ranges of from about 0 wt % to about 2 wt %, e.g., about 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, 1.1 wt %, 1.2 wt %, 1.3 wt %, 1.4 wt %, 1.5 wt %, 1.6 wt %, 1.7 wt %, 1.8 wt %, 1.9 wt %, 2.0 wt %. In certain exemplary embodiments, the composition does not comprise ethylhexyglycerin.

In certain exemplary embodiments, the concentrations of panthenol in the compositions of the present invention can include, but are not limited to, for example, concentrations in ranges of from about 0.1 wt % to about 1 wt %, e.g., about 0.1 wt %, 0.2 wt %, 0.3 wt %, 0.4 wt %, 0.5 wt %, 0.6 wt %, 0.7 wt %, 0.8 wt %, 0.9 wt %, 1.0 wt %. In certain exemplary embodiments, the composition does not comprise panthenol.

In certain exemplary embodiments, the concentrations of phenoxyethanol in the compositions of the present invention can include, but are not limited to, for example, concentrations in ranges of from about 0 wt % to about 1 wt %, e.g., about 0.1 wt %, 0.2 wt %, 0.3 wt %, 0.4 wt %, 0.5 wt %, 0.6 wt %, 0.7 wt %, 0.8 wt %, 0.9 wt %, 1.0 wt %. In certain exemplary embodiments, the composition does not comprise phenoxyethanol.

In certain exemplary embodiments, the concentrations of ethylhexyl stearate in the compositions of the present invention can include, but are not limited to, for example, concentrations in ranges of from about 0 wt % to about 1 wt %, e.g., about 0.1 wt %, 0.2 wt %, 0.3 wt %, 0.4 wt %, 0.5 wt %, 0.6 wt %, 0.7 wt %, 0.8 wt %, 0.9 wt %, 1.0 wt %. In certain exemplary embodiments, the composition does not comprise theylhexyl stearate.

In certain exemplary embodiments, the concentrations of Trideceth-6 in the compositions of the present invention can include, but are not limited to, for example, concentrations in ranges of from about 0 wt % to about 1 wt %, e.g., about 0.1 wt %, 0.2 wt %, 0.3 wt %, 0.4 wt %, 0.5 wt %, 0.6 wt %, 0.7 wt %, 0.8 wt %, 0.9 wt %, 1.0 wt %. In certain exemplary embodiments, the composition does not comprise Trideceth-6.

In certain exemplary embodiments, the concentrations of carbomer in the compositions of the present invention can include, but are not limited to, for example, concentrations in ranges of from about 0 wt % to about 2 wt %, e.g., about 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, 1.1 wt %, 1.2 wt %, 1.3 wt %, 1.4 wt %, 1.5 wt %, 1.6 wt %, 1.7 wt %, 1.8 wt %, 1.9 wt %, 2.0 wt %. In certain exemplary embodiments, the composition does not comprise carbomer.

In certain exemplary embodiments, the concentrations of acrylates/C10-30 (acrylates/C10-30 alkyl acrylate crosspolymer) in the compositions of the present invention can include, but are not limited to, for example, concentrations in ranges of from about 0 wt % to about 0.1 wt %, e.g., about 0.01 wt %, 0.02 wt %, 0.03 wt %, 0.04 wt %, 0.05 wt %, 0.06 wt %, 0.07 wt %, 0.08 wt %, 00.9 wt %, 0.1 wt %. In certain exemplary embodiments, the composition does not comprise acrylates/C10-30.

In certain exemplary embodiments, the concentrations of 1,2-hexanediol in the compositions of the present invention can include, but are not limited to, for example, concentrations in ranges of from about 0 wt % to about 2 wt %, e.g., about 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, 1.1 wt %, 1.2 wt %, 1.3 wt %, 1.4 wt %, 1.5 wt %, 1.6 wt %, 1.7 wt %, 1.8 wt %, 1.9 wt %, 2.0 wt %. In certain exemplary embodiments, the composition does not comprise 1,2-hexanediol.

In certain exemplary embodiments, the concentrations of sodium dodecylbenzenesulfonate in the compositions of the present invention can include, but are not limited to, for example, concentrations in ranges of from about 0 wt % to about 0.01 wt %, e.g., about 0.001 wt %, 0.002 wt %, 0.003 wt %, 0.004 wt %, 0.005 wt %, 0.006 wt %, 0.007 wt %, 0.008 wt %, 0.009 wt %, 0.010 wt %. In certain exemplary embodiments, the composition does not comprise sodium dodecylbenzenesulfonate.

In certain exemplary embodiments, the concentrations of sodium citrate in the compositions of the present invention can include, but are not limited to, for example, concentrations in ranges of from about 0 wt % to about 0.001 wt %, e.g., about 0.0001 wt %, 0.0002 wt %, 0.0003 wt %, 0.0004 wt %, 0.0005 wt %, 0.0006 wt %, 0.0007 wt %, 0.0008 wt %, 0.0009 wt %, 0.0010 wt %. In certain exemplary embodiments, the composition does not comprise sodium citrate.

In certain exemplary embodiments, the concentrations of silver sulfate in the compositions of the present invention can include, but are not limited to, for example, concentrations in ranges of from about 0 wt % to about 0.001 wt %, e.g., about 0.00005 wt %, about 0.0001 wt %, about 0.00015 wt %, 0.0002 wt %, about 0.00025 wt %, 0.0003 wt %, about 0.00035 wt %, 0.0004 wt %, about 0.00045 wt %, 0.0005 wt %, about 0.00055 wt %, 0.0006 wt %, about 0.00065 wt %, 0.0007 wt %, about 0.00075 wt %, 0.0008 wt %, about 0.00085 wt %, 0.0009 wt %, about 0.00095 wt %, 0.0010 wt %. In certain exemplary embodiments, the composition does not comprise silver sulfate.

In certain exemplary embodiments, the concentrations of silver in the compositions of the present invention can include, but are not limited to, for example, concentrations in ranges of from about 0 wt % to about 0.001 wt %, e.g., about 0.00005 wt %, about 0.0001 wt %, about 0.00015 wt %, 0.0002 wt %, about 0.00025 wt %, 0.0003 wt %, about 0.00035 wt %, 0.0004 wt %, about 0.00045 wt %, 0.0005 wt %, about 0.00055 wt %, 0.0006 wt %, about 0.00065 wt %, 0.0007 wt %, about 0.00075 wt %, 0.0008 wt %, about 0.00085 wt %, 0.0009 wt %, about 0.00095 wt %, 0.0010 wt %. In certain exemplary embodiments, the composition does not comprise silver.

In certain exemplary embodiments, the concentrations of benzyl alcohol in the compositions of the present invention can include, but are not limited to, for example, concentrations in ranges of from about 0 wt % to about 1 wt %, e.g., about 0.1 wt %, 0.2 wt %, 0.3 wt %, 0.4 wt %, 0.5 wt %, 0.6 wt %, 0.7 wt %, 0.8 wt %, 0.9 wt %, 1.0 wt %. In certain exemplary embodiments, the composition does not comprise benzyl alcohol.

In certain embodiments, the composition may further comprise one or more of additives such as moisturizers or humectants, germicidal or antiseptic agents, antioxidants, colorings, thickening agents, buffers, solvents, salts, polymers, essential oils, animal or plant extracts, gelling agents, silicones, vitamins, viscosity-reducing agents, fragrances, preservatives, penetration enhancers, acidity regulator, antioxidant, emulsifying agents, stinging agents, surfactants, ceramides, sunscreen ingredients, emollients, skin-conditioning agents, etc. Example additives include but are not limited to such as acrylates/C10-30 (acrylates/C10-30 alkyl acrylate crosspolymer), carbomer, 1,2-Hexanediol, sodium dodecylbenzenesulfonate, sodium citrate.

Non-limiting examples of preservatives include but are not limited to sodium benzoate, benzoic acid, sorbitol, phenoxyethanol, phenylethyl alcohol, benzalkonium chloride, EDTA, benzyl alcohol, potassium sorbate, parabens, chlorhexidine gluconate, and mixtures thereof.

Non-limiting examples of emollient include but are not limited to petrolatum (White Soft Paraffin), castor oil, cetyl alcohol, cetearyl alcohol, cocoa butter, isopropyl myristate, isopropyl palmitate, lanolin, liquid paraffin, polyethylene glycols, shea butter, silicone oils, stearic acid, and stearyl alcohol.

Non-limiting examples of antioxidants include but are not limited to vitamin C and vitamin E.

Optionally, detackifying agents may be added to the compositions of the present invention at an effective amount to reduce the stickiness or tack associated with humectants and/or gelling agents.

In certain embodiments, the composition, optionally, may further include at least one additional antimicrobial, antiviral or antifungal agent, or a combination thereof. Non-limiting examples of such agents include but are not limited to silver sulfate, silver, and benzyl alcohol.

In certain embodiments, the composition is unique in its combination of components that deliver good antiseptic performance (for example, meeting the requirements of EN 1276) and/or satisfactory results in toxicity (for example, meeting the Toxicological Risk Assessment (TRA) carried out according to the general principle of toxicology and taking reference of EU and US cosmetic regulations and standards).

US 12,629,322 B2

11

Numbered Embodiments—Set 1

1. An aqueous antiseptic composition comprising:
(a) glycerin about 8.5-16% by weight;
(b) caprylyl glycol about 0.45-3% by weight;
(c) acrylates/C10-30 about 0.01-0.1% by weight;
wherein the glycerin, the caprylyl glycol and the acrylates/C10-30 taken together form a first component, wherein the first component is more than about 13% by weight of the antiseptic composition.
2. An aqueous antiseptic composition, comprising:
(a) glycerin about 8.5-16% by weight;
(b) caprylyl glycol about 0.45-3% by weight; and
(c) ethoxydiglycol about 1-5% by weight;
wherein the glycerin, the caprylyl glycol and the ethoxydiglycol taken together form a first component, wherein the first component is more than about 13% by weight of the antiseptic composition.
3. The aqueous antiseptic composition of embodiments 1 or 2, wherein the first component further comprises phenoxyethanol about 0-1% by weight.
4. The aqueous aqueous antiseptic composition of embodiment 2, wherein the glycerin is about 8.5-10.7% by weight, the caprylyl glycol is about 0.6-1.3% by weight and the ethoxydiglycol is about 2.1-4.1% by weight of the antiseptic composition.
5. The aqueous antiseptic composition of embodiments 1 or 2, wherein the first component is less than about 25% by weight of the antiseptic composition and essentially free of alkyl glycerine and/or the alkyl ester thereof.
6. The aqueous antiseptic composition of embodiments 1 or 2, wherein the first component is less than about 25% by weight of the antiseptic composition and essentially free of ethylhexyglycerin.
7. The aqueous antiseptic composition of embodiments 1 or 2, further comprising one or more compounds selected from a group consisting of panthenol, sodium polyacrylate, phenoxyethanol, ethylhexyl stearate, and Trideceth-6.
8. The aqueous antiseptic composition of embodiment 7, wherein:
(a) the panthenol is about 0.1% to 1% by weight;
(b) the sodium polyacrylate is about 0.1% to 0.5% by weight;
(c) the phenoxyethanol is about 0 to 1% by weight;
(d) the ethylhexyl stearate is about 0 to 1% by weight; and
(e) the Trideceth-6 is about 0 to 1% by weight;
of the antiseptic composition.
9. The aqueous antiseptic composition of any one of the preceding embodiments, wherein the composition is essentially free of sodium polyacrylate.
10. The aqueous antiseptic composition of any one of the preceding embodiments, wherein the composition is essentially free of simple alcohols.
11. The aqueous antiseptic composition of any one of the preceding embodiments, wherein the composition further comprises about 0.01-0.1% acrylates/C10-30.
12. The aqueous antiseptic composition of any one of the preceding embodiments, wherein the first component further comprises about 0-2% ethylhexygkycerin.
13. The aqueous antiseptic composition of any one of the preceding embodiments, wherein the composition further comprises about 0.1-1% carbomer.
14. The aqueous antiseptic composition of any one of the preceding embodiments, wherein the composition further comprises about 1-5% 1, 2-hexanediol.

15. The aqueous antiseptic composition of any one of the preceding embodiments, wherein the composition further comprises one or more of the following: sodium dodecylbenzenesulfonate, sodium citrate, silver sulfate and silver.
16. The aqueous antiseptic composition of any one of the preceding embodiments, wherein the composition further comprises about 0-5% benzyl alcohol.
17. The aqueous antiseptic composition of any one of the preceding embodiments, wherein the composition has equal or greater biocidal efficacy and durability of bacterial inhibition than 75% isopropyl alcohol.
18. The aqueous antiseptic composition of any one of the preceding embodiments, wherein the composition is capable of exhibiting greater than a 4 log 10 kill of a microorganism within 5 minutes.
19. The aqueous antiseptic composition of any one of the preceding embodiments, wherein the composition is capable of exhibiting greater than a 6 log 10 kill of a virus within 30 seconds or within 1 minute.
20. The aqueous antiseptic composition of any one of the preceding embodiments, wherein the composition is effective in inhibition of COVID-19 within 5 minutes.
21. The aqueous antiseptic composition of any one of the preceding embodiments, wherein the composition does not substantially evaporate.
22. The aqueous antiseptic composition of any one of the preceding embodiments, wherein the composition remains on the surface to which it is applied for at least 1 minute, or at least 5 minutes.
23. The aqueous antiseptic composition of embodiment 18, wherein the microorganism is a bacterium, a fungus, a yeast, a mold, a virus or a combination thereof.
24. The aqueous antiseptic composition of embodiment 18, wherein the microorganism is a virus.
25. The aqueous antiseptic composition of embodiment 24, wherein the virus is H3N2 influenza A virus.
26. The aqueous antiseptic composition of embodiment 24, wherein the virus is a human coronavirus.
27. The aqueous antiseptic composition of embodiment 26, wherein the human coronavirus is strain 229 E or COVID-19.
28. The aqueous antiseptic composition of embodiment 18, wherein the microorganism is one or more of *Escherichia coli, Staphylococcus aureus, Candida albicans*, H3N2 influenza A or virus human coronavirus.
29. A skin or hand sanitizer comprising the aqueous antiseptic composition of any one of the preceding embodiments.
30. An aqueous antiseptic surface coating comprising the aqueous antiseptic composition of any one of the preceding embodiments.
31. A woven or non-woven wipe, sponge, or tissue, comprising the aqueous antiseptic composition of any one of the preceding embodiments.
32. An aqueous antiseptic composition, comprising:
(a) a polyol about 8-20% by weight;
(b) a glycol about 1-5% by weight and/or an aromatic alcohol about 0-5% by weight;
wherein a sum of the polyol, the glycol and the aromatic alcohol is about 13-25% by weight of the composition; and
the composition is substantially free of alkyl glycerine and the alkyl ester thereof, and free of simple alcohols.

33. The aqueous antiseptic composition of embodiment 26, wherein the polyol is glycerin about 8.5-16% by weight and caprylyl glycol about 0.45-3% by weight.

34. The aqueous antiseptic composition of embodiment 26, wherein the glycol is ethoxydiglycol about 2.06-4.12%.

35. The aqueous antiseptic composition of embodiment 26, wherein the aromatic alcohol is one of more of phenoxyethanol, benzyl alcohol and phenethyl alcohol.

36. The aqueous antiseptic composition of embodiment 27, wherein the polyol is about 1-2% 1,2-Hexanediol.

37. The aqueous antiseptic composition of embodiment 27, further comprising silver and/or silver ions.

38. Use of an aqueous antiseptic composition of any one of the preceding embodiments in the manufacture of a sanitizer.

39. A aqueous non-alcoholic sanitizer, comprising:
(a) glycerin about 8.5-16% by weight;
(b) caprylyl glycol about 0.45-3% by weight;
(c) acrylates/C10-30 about 0.01-0.1% by weight; and
wherein a sum of the glycerin, the caprylyl glycol, and the acrylates/C10-30 is about 13-25% by weight of the sanitizer.

40. The aqueous non-alcoholic sanitizer of embodiment 39, wherein the sanitizer further comprises one or more compounds selected from the group consisting of phenoxyethanol about 0-1% by weight, panthenol about 0.1-1% by weight, sodium polyacrylate about 0-0.5% by weight, ethylhexyl stearate about 0-1% by weight, Trideceth-6 about 0-1% by weight and carbomer about 0.1-1% by weight.

41. The aqueous non-alcoholic sanitizer of embodiment 39, wherein the sanitizer is essentially free of alkyl glycerin and/or the alkyl ester thereof.

42. The aqueous non-alcoholic sanitizer of embodiment 39, wherein the sanitizer is essentially free of ethylhexyglycerin.

43. The aqueous non-alcoholic sanitizer of embodiment 39, wherein the sum of glycerin, the caprylyl glycol and the acrylates/C10-30 is about 15% by weight.

44. The aqueous non-alcoholic sanitizer of embodiment 43, further comprising panthenol about 0.3% by weight, phenoxyethanol about 0.5% by weight and carbomer about 0.8% by weight.

45. The aqueous non-alcoholic sanitizer of embodiment 43, further comprising panthenol about 0.3% by weight, sodium polyacrylate about 0.4% by weight, ethylhexyl stearate about 0.2% by weight, Trideceth-6 about 0.07% by weight, and carbomer about 0.1% by weight.

46. An aqueous non-alcoholic sanitizer, comprising:
(a) glycerin about 8.5-16% by weight;
(b) caprylyl glycol about 0.45-3% by weight; and
(c) ethoxydiglycol about 1-5% by weight;
wherein a sum of the glycerin, the caprylyl glycol, and the ethoxydiglycol is about 13-25% by weight of the sanitizer.

47. The aqueous non-alcoholic sanitizer of embodiment 46, wherein the sum of the glycerin, the caprylyl glycol and the ethoxydiglycol is about 19% by weight.

48. The aqueous non-alcoholic sanitizer of embodiment 46, further comprising phenoxyethanol about 0.5% by weight, panthenol about 0.3% by weight, sodium polyacrylate about 0.2% by weight; ethylhexyl stearate about 0.09% by weight; Trideceth-6 about 0.03% by weight; and ethylhexyglycerin about 0.9% by weight.

49. The aqueous non-alcoholic sanitizer of embodiment 46, further comprising panthenol about 0.3% by weight, sodium polyacrylate about 0.2% by weight; ethylhexyl stearate about 0.11% by weight; Trideceth-6 about 0.04% by weight; ethylhexyglycerin about 0.9% by weight and 1,2-Hexanediol about 1.5% by weight.

50. The aqueous non-alcoholic sanitizer of embodiment 46, wherein the sum of the glycerin, the caprylyl glycol and the ethoxydiglycol is about 16.4% by weight.

51. The aqueous non-alcoholic sanitizer of embodiment 46, further comprising the phenoxyethanol about 0.5% by weight, panthenol about 0.3% by weight, sodium polyacrylate about 0.3% by weight; ethylhexyl stearate about 0.09% by weight; Trideceth-6 about 0.03% by weight.

52. The aqueous non-alcoholic sanitizer of embodiment 47, further comprising sodium dodecylbenzene-sulfonate about 0.005% by weight, sodium citrate about 0.0006% by weight, silver sulfate about 0.00015% by weight and silver about 0.00015% by weight.

53. The aqueous non-alcoholic sanitizer of embodiment 52, further comprising benzyl alcohol about 1% by weight.

54. The aqueous non-alcoholic sanitizer of embodiment 42, wherein the sum of the glycerin, the caprylyl glycol and the ethoxydiglycol is about 20.8% by weight.

55. The aqueous non-alcoholic sanitizer of embodiment 54, further comprising phenoxyethanol about 0.5% by weight, panthenol about 0.3% by weight, sodium polyacrylate about 0.2% by weight; ethylhexyl stearate about 0.11% by weight; and Trideceth-6 about 0.04% by weight.

56. Use of the composition of any one of the preceding embodiments for the manufacture of a medicament for treating dermatitis.

Numbered Embodiments—Set 2

1. An aqueous antiseptic composition comprising
(a) glycerin about 8.5-16% by weight;
(b) caprylyl glycol about 0.45-3% by weight; and
(c) a first ingredient;
wherein the first ingredient is selected from a group consisting of acrylates/C10-30 about 0.01-0.1% by weight and ethoxydiglycol about 1-5% by weight, and the glycerin, the caprylyl glycol and the first ingredient taken together is more than about 13% by weight of the antiseptic composition.

2. The aqueous antiseptic composition of embodiment 1, further comprising phenoxyethanol about 0-1% by weight.

3. The aqueous antiseptic composition of embodiment 1, wherein the glycerin is about 8.5-10.7% by weight, the caprylyl glycol is about 0.6-1.3% by weight and the first ingredient is ethoxydiglycol and is about 2.1-4.1% by weight of the antiseptic composition.

4. The aqueous antiseptic composition of embodiment 1, wherein the glycerin, the caprylyl glycol and the first ingredient are less than about 25% by weight of the antiseptic composition and essentially free of alkyl glycerine and/or the alkyl ester thereof.

5. The aqueous antiseptic composition of embodiment 1, wherein the glycerin, the caprylyl glycol and the first ingredient are less than about 25% by weight of the antiseptic composition and essentially free of ethylhexyglycerin.

6. The aqueous antiseptic composition of embodiment 1, further comprising one or more compounds selected from a group consisting of panthenol, sodium polyacrylate, phenoxyethanol, ethylhexyl stearate, and Trideceth-6.

7. The aqueous antiseptic composition of embodiment 6, wherein
the panthenol is about 0.1% to 1% by weight;
the sodium polyacrylate is about 0.1% to 0.5% by weight;
the phenoxyethanol is about 0 to 1% by weight;
the ethylhexyl stearate is about 0 to 1% by weight; and
the Trideceth-6 is about 0 to 1% by weight;
of the antiseptic composition.

8. The aqueous antiseptic composition of embodiment 1, wherein the glycerin, the caprylyl glycol and the first ingredient are less than about 25% by weight of the antiseptic composition and essentially free of phenoxyethanol.

9. The aqueous antiseptic composition of embodiment 8, further comprising one or more compounds selected from a group consisting of panthenol, sodium polyacrylate, ethylhexyl stearate, trideceth-6, ethylhexylglycerin, 1,2-hexanediol.

10. The aqueous antiseptic composition of embodiment 9, wherein
the panthenol is about 0.1% to 1% by weight;
the sodium polyacrylate is about 0.1% to 0.5% by weight;
the ethylhexyl stearate is about 0 to 1% by weight; and
the Trideceth-6 is about 0 to 1% by weight;
of the antiseptic composition.

11. The aqueous antiseptic composition of any one of the preceding embodiments, wherein the composition is essentially free of sodium polyacrylate.

12. The aqueous antiseptic composition of any one of the preceding embodiments, wherein the composition is essentially free of simple alcohols.

13. The aqueous antiseptic composition of any one of the preceding embodiments, wherein the composition further comprises about 0.01-0.1% acrylates/C10-30.

14. The aqueous antiseptic composition of any one of the preceding embodiments, wherein the composition further comprises about 0-2% ethylhexyglycerin.

15. The aqueous antiseptic composition of any one of the preceding embodiments, wherein the composition further comprises about 0.1-1% carbomer.

16. The aqueous antiseptic composition of any one of the preceding embodiments, wherein the composition further comprises about 1-5% 1, 2-hexanediol.

17. The aqueous antiseptic composition of any one of the preceding embodiments, wherein the composition further comprises one or more of the following: sodium dodecylbenzenesulfonate, sodium citrate, silver sulfate and silver.

18. The aqueous antiseptic composition of any one of the preceding embodiments, wherein the composition further comprises about 0-5% benzyl alcohol.

19. The aqueous antiseptic composition of any one of the preceding embodiments, further comprising *Avena sativa* (Oat) Kernel Flour.

20. The aqueous antiseptic composition of any one of the preceding embodiments, wherein the composition has equal or greater biocidal efficacy and durability of bacterial inhibition than 75% isopropyl alcohol.

21. The aqueous antiseptic composition of any one of the preceding embodiments, wherein the composition is capable of exhibiting greater than a 4 log 10 kill of a microorganism within 5 minutes.

22. The aqueous antiseptic composition of any one of the preceding embodiments, wherein the composition is capable of exhibiting greater than a 6 log 10 kill of a virus within 30 seconds or within 1 minute.

23. The aqueous antiseptic composition of any one of the preceding embodiments, wherein the composition is effective in inhibition of COVID-19 within 5 minutes.

24. The aqueous antiseptic composition of any one of the preceding embodiments, wherein the composition does not substantially evaporate.

25. The aqueous antiseptic composition of any one of the preceding embodiments, wherein the composition remains on the surface to which it is applied for at least 1 minute, or at least 5 minutes.

26. The aqueous antiseptic composition of embodiment 25, wherein the microorganism is a bacterium, a fungus, a yeast, a mold, a virus or a combination thereof.

27. The aqueous antiseptic composition of embodiment 25, wherein the microorganism is a virus.

28. The aqueous antiseptic composition of embodiment 27, wherein the virus is H3N2 influenza A virus.

29. The aqueous antiseptic composition of embodiment 27, wherein the virus is a human coronavirus.

30. The aqueous antiseptic composition of embodiment 29, wherein the human coronavirus is strain 229 E or COVID-19.

31. The aqueous antiseptic composition of embodiment 26, wherein the microorganism is one or more of *Escherichia coli, Staphylococcus aureus, Candida albicans*, H3N2 influenza A virus and human coronavirus.

32. A skin or hand sanitizer comprising the aqueous antiseptic composition of any one of the preceding embodiments.

33. An aqueous antiseptic surface coating comprising the aqueous antiseptic composition of any one of the preceding embodiments.

34. A woven or non-woven wipe, sponge, or tissue, comprising the aqueous antiseptic composition of any one of the preceding embodiments.

35. An aqueous antiseptic composition, comprising
a polyol about 8-20% by weight;
a glycol about 1-5% by weight and/or an aromatic alcohol about 0-5% by weight;
wherein a sum of the polyol, the glycol and the aromatic alcohol is about 13-25% by weight of the composition; and
the composition is substantially free of alkyl glycerine and the alkyl ester thereof, and substantially free of simple alcohols.

36. The aqueous antiseptic composition of embodiment 35, wherein the polyol is glycerin about 8.5-16% by weight and caprylyl glycol about 0.45-3% by weight.

37. The aqueous antiseptic composition of embodiment 35, wherein the glycol is ethoxydiglycol about 2.06-4.12%.

38. The aqueous antiseptic composition of embodiment 35, wherein the aromatic alcohol is one or more of phenoxyethanol, benzyl alcohol and phenethyl alcohol.

39. The aqueous antiseptic composition of embodiment 35, wherein the polyol is about 1-2% 1,2-Hexanediol.

40. The aqueous antiseptic composition of embodiment 35, further comprising silver and/or silver ions.

41. Use of the aqueous antiseptic composition of any one of the preceding embodiments in the manufacture of a sanitizer.

42. An aqueous non-alcoholic sanitizer, comprising
glycerin about 8.5-16% by weight;
caprylyl glycol about 0.45-3% by weight; and
a first ingredient;
wherein the first ingredient is selected from a group
   consisting of acrylates/C10-30 about 0.01-0.1% by
   weight and ethoxydiglycol about 1-5% by weight, and
a sum of the glycerin, the caprylyl glycol, and the first
   ingredient is about 13-25% by weight of the sanitizer.

43. The aqueous non-alcoholic sanitizer of embodiment
   42, wherein the sanitizer further comprises one or more
   compounds selected from the group consisting of phe-
   noxyethanol about 0-1% by weight, panthenol about
   0.1-1% by weight, sodium polyacrylate about 0-0.5%
   by weight, ethylhexyl stearate about 0-1% by weight,
   Trideceth-6 about 0-1% by weight and carbomer about
   0.1-1% by weight.

44. The aqueous non-alcoholic sanitizer of embodiment
   42, wherein the sanitizer is essentially free of alkyl
   glycerin and/or the alkyl ester thereof.

45. The aqueous non-alcoholic sanitizer of embodiment
   42, wherein the sanitizer is essentially free of ethyl-
   hexyglycerin.

46. The aqueous non-alcoholic sanitizer of embodiment
   42, wherein the first ingredient is acrylates/C10-30 and
   the sum of glycerin, the caprylyl glycol and the acry-
   lates/C10-30 is about 15% by weight.

47. The aqueous non-alcoholic sanitizer of embodiment
   42, further comprising panthenol about 0.3% by
   weight, phenoxyethanol about 0.5% by weight and
   carbomer about 0.8% by weight.

48. The aqueous non-alcoholic sanitizer of embodiment
   42, further comprising panthenol about 0.3% by
   weight, sodium polyacrylate about 0.4% by weight,
   ethylhexyl stearate about 0.2% by weight, Trideceth-6
   about 0.07% by weight, and carbomer about 0.1% by
   weight.

49. The aqueous non-alcoholic sanitizer of embodiment
   42, wherein the first ingredient is ethoxydiglycol and
   the sum of glycerin, the caprylyl glycol and the ethoxy-
   diglycol is about 19% by weight.

50. The aqueous non-alcoholic sanitizer of embodiment
   42, further comprising phenoxyethanol about 0.5% by
   weight, panthenol about 0.3% by weight, sodium poly-
   acrylate about 0.2% by weight; ethylhexyl stearate
   about 0.09% by weight; Trideceth-6 about 0.03% by
   weight; and ethylhexyglycerin about 0.9% by weight.

51. The aqueous non-alcoholic sanitizer of embodiment
   42, further comprising panthenol about 0.3% by
   weight, sodium polyacrylate about 0.2% by weight;
   ethylhexyl stearate about 0.11% by weight; Trideceth-6
   about 0.04% by weight; ethylhexyglycerin about 0.9%
   by weight and 1,2-hexanediol about 1.5% by weight.

52. The aqueous non-alcoholic sanitizer of embodiment
   42, wherein the first ingredient is ethoxydiglycol and
   the sum of the glycerin, the caprylyl glycol and the
   ethoxydiglycol is about 16.4% by weight.

53. The aqueous non-alcoholic sanitizer of embodiment
   52, further comprising the phenoxyethanol about 0.5%
   by weight, panthenol about 0.3% by weight, sodium
   polyacrylate about 0.3% by weight; ethylhexyl stearate
   about 0.09% by weight; Trideceth-6 about 0.03% by
   weight.

54. The aqueous non-alcoholic sanitizer of embodiment
   53, further comprising sodium dodecylbenzene-
   sulfonate about 0.005% by weight, sodium citrate about 0.0006% by weight, silver sulfate about
0.00015% by weight and silver about 0.00015% by
weight.

55. The aqueous non-alcoholic sanitizer of embodiment
   54, further comprising benzyl alcohol about 1% by
   weight.

56. The aqueous non-alcoholic sanitizer of embodiment
   42, wherein the first ingredient is ethoxydiglycol and
   the sum of the glycerin, the caprylyl glycol and the
   ethoxydiglycol is about 20.8% by weight.

57. The aqueous non-alcoholic sanitizer of embodiment
   56, further comprising phenoxyethanol about 0.5% by
   weight, panthenol about 0.3% by weight, sodium poly-
   acrylate about 0.2% by weight; ethylhexyl stearate
   about 0.11% by weight; and Trideceth-6 about 0.04%
   by weight.

58. The aqueous non-alcoholic sanitizer of embodiment
   42, wherein the first ingredient is ethoxydiglycol and
   the sum of the glycerin, the caprylyl glycol and the
   ethoxydiglycol is about 17.4-19.0% by weight.

59. The aqueous non-alcoholic sanitizer of embodiment
   58, further comprising one or more compounds
   selected from a group consisting of panthenol, sodium
   polyacrylate, ethylhexyl stearate, trideceth-6, ethylhex-
   ylglycerin, 1,2-hexanediol.

60. The aqueous antiseptic composition of embodiment
   59, wherein the panthenol is about 0.1% to 1% by weight;

the sodium polyacrylate is about 0.1% to 0.5% by weight;

the ethylhexyl stearate is about 0 to 1% by weight;

the Trideceth-6 is about 0 to 1% by weight;

the ethylhexylglycerin is about 0 to 2% by weight; and the 1,2hexanediol is about 1 to 5% by weight;

of the antiseptic composition.

61. Use of the composition or sanitizer of any one of the
   preceding embodiments for the manufacture of a medi-
   cament for treating skin condition (e.g., dermatitis).

62. A method of alleviating or treating at least one skin
   condition in a subject in need thereof, comprising:
   administering a therapeutically or prophylactically
   effective amount of the composition or the sanitizer of
   any one of the preceding embodiments to the subject to
   treat the skin condition.

63. The method of embodiment 62, wherein the skin
   condition is dermatitis.

64. The method of embodiment 62, wherein the skin
   condition is selected from a group consisting of
   eczematous blisters, skin dryness, skin thickening, skin
   thinning, skin cracks, skin flakiness, skin inflammation,
   itchy skin, dyshidrotic eczema, irritant contact derma-
   titis, skin allergies to alcohol, skin flakiness, skin
   cracks, skin stiffness, atopic dermatitis, irritant contact
   dermatitis, and erythema.

65. The method of embodiment 62, wherein the compo-
   sition or sanitizer is administered topically.

66. A method of killing a microorganism within 30
   seconds to 1 minute by contacting the microorganism
   with the composition or the sanitizer of any one of the
   preceding embodiments.

67. The method of embodiment 66, wherein the micro-
   organism is one or more of *Escherichia coli*, *Staphy-*

*lococcus aureus, Candida albicans*, H3N2 influenza A virus or human coronavirus (e.g., COVID-19).

EXAMPLES

The following examples are not intended to limit the scope of the invention, but are only intended to be exemplary in nature.

Example 1

Formulations and Methods of Making

TABLE 1.1

Exemplary compositions in accordance with the present invention. The following compositions were formulated (proportion is in percentage (%) by weight) as described in Table 1.1.

| | Composition | | | | | | |
| | % by weight | | | | | | |
| Compound | A | B | C | D | E | F | G |
| --- | --- | --- | --- | --- | --- | --- | --- |
| Glycerin | 14.47 | 13.01 | 15.386 | 13.01 | 12.5 | 12.5 | 14.47 |
| Caprylyl glycol | 0.45 | 2.947 | 1.26 | 2.947 | 0.9 | 0.9 | 0.45 |
| Ethoxydiglycol | — | 3.09 | 4.12 | 3.09 | 3 | 3 | — |
| Panthenol | 0.3 | 0.3 | 0.282 | 0.3 | 0.3 | 0.3 | 0.3 |
| Sodium polyacrylate | — | 0.18 | 0.226 | 0.21 | 0.33 | 0.33 | 0.414 |
| Acrylates/C10-30 | 0.03 | — | — | — | — | — | 0.03 |
| Phenoxyethanol | 0.5 | 0.5 | 0.471 | — | 0.5 | 0.5 | 0.5 |
| Ethylhexyl stearate | — | 0.09 | 0.113 | 0.105 | 0.09 | 0.09 | 0.207 |
| Trideceth-6 | — | 0.03 | 0.038 | 0.035 | 0.03 | 0.03 | 0.069 |
| Ethylhexylglycerin | — | 0.858 | 0.113 | 0.858 | — | — | — |
| Carbomer | 0.75 | — | — | — | — | — | 0.12 |
| 1,2-Hexanediol | — | — | — | 1.5 | — | — | — |
| Sodium Dodecylbenzenesulfonate | — | — | — | — | 0.005 | — | — |
| Sodium Citrate | — | — | — | — | 0.0006 | — | — |
| Silver Sulfate | — | — | — | — | 0.00015 | — | — |
| Silver | — | — | — | — | 0.00015 | — | — |
| Benzyl alcohol | — | — | — | — | — | 1 | — |
| water | Up to 100 | Up to 100 | Up to 100 | Up to 100 | Up to 100 | Up to 100 | Up to 100 |

In certain exemplary embodiments, the composition contains glycerin, caprylyl glycol and a first ingredient, wherein the first ingredient is acrylates/C10-30 and/or ethoxydiglycol. Glycerin, caprylyl glycol and the first ingredient together form the first component. In certain exemplary embodiments and as seen in Compositions A and G above, the compositions may contain about 14.47% glycerin by weight, about 0.45% caprylyl glycol by weight, about 0.03% acrylates/C10-30 by weight and water up to 100%. In these embodiments, the compositions does not contain ethoxydiglycol. In a further exemplary embodiment and as seen in Composition A, the formula may further contain about 0.3% panthenol by weight, about 0.5% phenoxyethanol by weight and about 0.75% carbomer by weight. In this exemplary embodiment, the composition does not contain sodium polyacrylate. In a further exemplary embodiment and as seen in Composition G, the composition may further contain about 0.3% panthenol by weight, about 0.414% sodium polyacrylate by weight, about 0.5% phenoxyethanol by weight, about 0.207% ethylhexyl stearate by weight, about 0.069% Trideceth-6 by weight and about 0.12% carbomer by weight.

In certain exemplary embodiments and as seen in Compositions B and D above, the compositions may contain about 13.01% glycerin by weight, about 2.947% caprylyl glycol by weight and about 3.09% ethoxydiglycol by weight and water up to 100%. In a further exemplary embodiment and as seen in Composition B, the composition may further contain about 0.3% panthenol by weight, about 0.18% sodium polyacrylate by weight, about 0.5% phenoxyethanol by weight, about 0.09% ethylhexyl stearate by weight, about 0.03% Trideceth-6 by weight and about 0.858% ethylhexylglycerin by weight. In a further exemplary embodiment and as seen in Composition D, the composition may further contains about 0.3% panthenol by weight, about 0.21% sodium polyacrylate by weight, about 0.105% ethylhexyl stearate by weight, about 0.035% Trideceth-6 by weight, about 0.858% ethylhexylglycerin by weight and about 1.5% 1,2-hexanediol by weight. In this exemplary embodiment, the composition does not contain phenoxyethanol.

In certain exemplary embodiments and as seen in Composition C above, the compositions may contain about 15.386% glycerin by weight, about 1.26% caprylyl glycol by weight and about 4.12% ethoxydiglycol by weight and water up to 100%. In a further exemplary embodiment and as seen in Composition C, the composition may further contain about 0.282% panthenol by weight, about 0.226% sodium polyacrylate by weight, about 0.471% phenoxyethanol by weight, about 0.113% ethylhexyl stearate by weight, about 0.038% Trideceth-6 by weight, and about 0.113% ethylhexylglycerin by weight.

In certain exemplary embodiments and as seen in Compositions E and F above, the compositions may contain about 12.5% glycerin by weight, about 0.9% caprylyl glycol by weight and about 3% ethoxydiglycol by weight and water up to 100%. In a further exemplary embodiment, the compositions may further contain about 0.3% panthenol by weight, about 0.33% sodium polyacrylate by weight, about 0.5% phenoxyethanol by weight, about 0.09% ethylhexyl stearate by weight and about 0.03% Trideceth-6 by weight. In a further exemplary embodiment and as seen in composition E, the composition may further contain about 0.005% sodium dodecylbenzenesulfonate by weight, about 0.0006% sodium citrate by weight, about 0.00015% silver sulfate by weight and about 0.00015% silver. In yet another exemplary embodiment and as seen in composition F, the composition may further contain about 1% benzyl alcohol by weight 1. Method of Making Example Formulations The ingredients and percentages used to prepare the exemplary compositions are set forth in Table 1. In certain exemplary embodiments, all ingredients may be mixed together in water under moderate mechanical agitation until homogenous. If necessary, the mixture is agitated with a suitable elevated temperature, for example, 30° C.-60° C. The pH of the final composition may be adjusted to about 5-7 with suitable pH modifiers, such as sodium hydroxide or sodium citrate.

In other exemplary embodiments, the gelling agents (such as carbomer) and/or thickening agents (such as sodium polyacrylate or acrylates/C10-30) may be heated at suitable elevated temperatures (for example, at about 60° C.) in a suitable amount of water under slow mechanical agitation in order to obtain a Phase 1. Then, the rest of the ingredients may be dissolved at another suitable temperature (such as about 40° C.) in a suitable amount of water under stirring in order to obtain a Phase 2. In a further exemplary embodiment, if certain ingredients are temperature sensitive, these ingredients may be separately prepared as Phase 3 (or more phases) at a suitable temperature (such as ambient). In order to obtain the final product, Phase 1 and Phase 2 are mixed together under moderate agitation. When the temperature of the gel reaches a suitable temperature (such as ambient), Phase 3 is added. The pH may be adjusted to about 5-7 with pH modifiers, such as sodium hydroxide or sodium citrate.

Example 2

Methods and Materials

Bactericidal and Fungicidal Efficacy Test

The bactericidal and fungicidal efficacy of the exemplary compositions are tested with the Suspension quantitative killing test and Fungal killing test methods according to sections 2.1.1.7.4 and 2.1.1.7.9 of Technical Standard for Disinfection (Ministry of Health of the People's Republic of China, 2002), which is incorporated herein by reference.

Suspension quantitative killing test 2.1.1.7.4 operation procedures:
  (1) First the disinfectant solution is prepared according to the requirements of the product manual. Unless otherwise specified, sterile hard water is used to prepare, the concentration of the preparation is 1.25 times the concentration to be tested (for example, the concentration of the disinfectant to be evaluated is 200 mg/L, it should be prepared 250 mg/L), set in 20° C.±1° C. water bath for use.
  (2) The experimental bacterial suspension to be tested is prepared, with a concentration of $1\times10^8$ cfu/ml to $5\times10^8$ cfu/ml.
  (3) 0.5 ml of test bacterial suspension is added first, then 0.5 ml of an organic interfering substance is added, mix well, and the mixture is incubated in 20° C.±1° C. water bath for 5 min. Then, transfer 4.0 ml of the prepared disinfectant solution into the mixture with a sterile transfer pipette, the mixture is mixed quickly and the time is recorded immediately.
  (4) The test bacteria and the disinfectant is allowed to react until each predetermined time, then 0.5 ml of the mixed solution of test bacteria and disinfectant is transferred and mixed with 4.5 ml of sterilized neutralizer, and the solution is mixed well.
  (5) After the mixed solution of test bacteria and disinfectant in each tube is added with a neutralizer for 10 minutes, 1.0 ml of the sample liquid is drawn respectively, and determine the number of viable bacteria count according to the viable bacteria culture plate counting method. For each sample liquid, inoculate 2 agar plates. If the number of colonies growing on the plate is too much, a series of 10-fold dilutions can be performed so that the viable bacterial culture can be counted.
  (6) Simultaneously, a positive control is prepared by using the diluent to replace the disinfectant.
  (7) All test samples are cultivated in a 37° C. incubator, and the final results are observed after culturing the bacterial cultures for 48 hours. For bacterial spores, the test samples need to be cultured for 72 hours to observe the final results.
  (8) The tests are repeated in triplicate, and the viable bacterial concentration (cfu/ml) of each group is calculated, and the results are converted to the logarithmic value (N), then the logarithmic value of killing is calculated according to the following formula: killing log value (KL)=Logarithmic value of average viable bacterial concentration (No) of Control group–Logarithmic value of viable bacterial concentration of Test group (Nx). When calculating the logarithmic value of killing, two digits after the decimal point can be used to round off numbers. If the average number of colonies produced after disinfection in the disinfection test group is less than or equal to 1, the logarithmic value of its killing is greater than or equal to the logarithm of the average viable bacterial concentration of the control group before the test.

Fungal Killing Test 2.1.1.9 Operation Procedures:

The test is to verify the dose of the disinfectant in the suspension or on the carrier required to kill fungal cultures or fungal spores in the laboratory, in order to prove the effective disinfection dose for fungi and their spores.

Testing equipment/materials
  (1) Malt extract agar (MEA).
  (2) Sandcastle agar medium.
  (3) Preparation of test microorganism and their suspensions or pellets
  Candida albicans ATCC 10231 and/or Aspergillus niger ATCC 16404 or spore suspensions and their pellets.
  In addition, according to the specific use and special needs of the disinfectant, other fungal or spore suspensions and pellets can be selected.
  (4) Neutralizer.
  (5) Phosphate buffer (PBS, 0.03 mol/L, pH 7.2).
  (6) Hard water for disinfectant dilution.
  (7) Organic interfering substance.
  (8) Scale pipettes (0.1 ml, 1.0 ml, 5.0 ml).
  (9) Constant temperature water bath.
  (10) Spray device (for spray disinfection test).
  (11) Electric mixer.
  (12) Timing device.

2.1.1.9.3 Preparation of Fungal Suspension
(1) Preparation of Candida albicans Suspension
  1) The freeze-dried fungus seed tube is taken, and opened with aseptic techniques, an appropriate amount of sandcastle liquid culture medium is transferred to a tube with a capillary pipette. The culture is pipetted up and down several times to disperse the culture. A test tube containing 5.0 ml~10.0 ml sandcastle liquid culture medium is prepared, and added a few drops of the strain suspension. The culture is incubated at 37° C. for 18 to 24 hours. The suspension of the first-generation culture is taken with the inoculation loop, and streaked on the sandcastle agar medium. The agar medium is incubated at 37° C. for 18 to 24 hours. The typical colonies in the second-generation culture are selected and inoculated on the slope of sand castle agar. The agar is cultured at 37° C. for 18 h to 24 h to form the third-generation culture. The culture is stored at 4° C. after sealing, and the using time should not exceed 6 weeks.

2) During the experiment, the third-generation culture is continuously passaged on the sandcastle agar slant using the same method as for preparing the third generation. The fresh, fifth or sixth generation sand-castle agar medium slant fresh culture (18 h~24 h) is used. 3.0 ml-5.0 ml of the diluent is pipetted to the slant culture tube using a 5.0 ml pipette, and the diluent is repeatedly pipetted up and down to wash the culture. Subsequently, the wash solution is transferred to another sterile test tube and mixed for 20 seconds, or tap 80 times on the palm to make the *Candida albicans* suspension homogeneous.

3) In the suspension sterilization test, the fungal count of the experimental suspension is $1\times10^7$ cfu/ml~$5\times10^7$ cfu/ml.

4) The fungal suspension is stored in the refrigerator at 4° C. for future use within the day. Overnight culture will not be used.

5) When contamination is suspected, identification should be carried out by methods such as colony morphology, Gram staining, and biochemical tests. Colony morphology can be directly observed with a microscope. The morphology of the fungus can be directly observed with a high-power microscope after smearing, or it can be stained by the ink shade method (the culture is mixed with black ink on a glass slide and smeared into a film) and observed.

(2) Preparation of *Aspergillus niger* ATCC 16404 Suspension or Pellets.

1) The freeze-dried fungus seed tube is taken, and opened by aseptic techniques, a small amount of malt extract broth medium is pipetted and added to the fungus. The culture is pipetted gently in the seed tube to disperse the cultural sediment. A little amount of the sediment suspension is added to a test tube having 5.0 ml malt extract broth medium, and is incubated at 30° C.±1° C. for 42-48 hours. The first-generation culture is inoculated to the MEA agar and incubated at 30° C.±1° C. in an incubator for 42-48 hours. A typical colony in culture plate is selected and inoculated in the malt extract nutrient agar slant medium. The slant culture was incubated at 30° C.±1° C. in an incubator for 42-48 hours, which becomes the third generation culture. The culture is stored at 4° C. after sealing, and used within 9 weeks.

2) During the test, the third-generation slant culture is inoculated to the malt extract agar slant and incubated at 30° C. for 48 hours. 3.0-5.0 ml malt extract broth is used to wash the culture on the slant, and inoculated to the Roche bottle, and shake to make the culture spread cover the surface of the MEA medium. Then the excess broth culture liquid is aspirated and the Roche bottle is incubated at 30° C.±1° C. for 7-9 days.

3) 5.0 ml to 10.0 ml of 0.05% (V/V) Tween 80 saline solution is added to the Roche bottle culture, and the spores of *Aspergillus niger* are scraped and washed in the solution. The spore suspension is transferred into a triangular flask with glass beads, and shaked gently for 1 minute. The mycelium is filter removed. After filtration, the suspension is observed under a microscope (400 times) to check the presence of mycelium. If mycelium is present in the suspension, the suspension can be centrifuged at 5000 r/min~6000 r/min for 20 min. The suspension is observed under the microscope (400 times) again and see if the mycelium is still present in the suspension. If mycelium is still present in the suspension, the suspension must be centrifuged again.

4) The fungal suspension of *Aspergillus niger* should be stored at 2° C.-8° C. but not for more than 2 days. Before use, the suspension is mixed evenly and observe whether there are spores sprouting under the microscope (400 times). If spores are sprouting, discard them.

5) When used, it can be properly diluted with diluent. During the suspension test, the spore content of the experimental fungal suspension is $1\times10^7$ cfu/ml-$5\times10^7$ cfu/ml.

6) The method of staining when preparing the staining sample is the drip staining method. 10 µl of fungal suspension is added to each piece. After staining the fungus, it is dried in a 37° C. incubator (approximately 30 min), or dry at room temperature before use.

7) The number of recovered fungus should reach $5\times10^5$ cfu/piece-$5\times10^6$ cfu/piece, which can be determined according to test requirements.

2.1.1.9.4 Test Group

The tests are divided into the following groups:

(1) The test group, according to the provisions of 2.1.1.7.3, select the disinfectant concentration and action time to test for the efficacy of killing to the tested strain.

(2) For the positive control group, the disinfectant solution is replaced with hard water, and the test is performed according to the procedure specified in 2.1.1.7.3. The results represent the initial concentration of test strain contained in the test system, and the logarithmic value of the disinfection factor for the test strain is calculated.

(3) Negative control group, to check whether the relevant solutions for test and media used in the same experiment are contaminated.

2.1.1.9.5 Test Procedure

The medium to be used is sand castle dextrose agar for *Candida albicans* and malt extract agar (MEA) for *Aspergillus niger*. Please refer to 2.1.1.7 for the operation procedure.

When counting viable count, *C. albicans* was cultured in a 37° C. incubator for 48 hours to observe the final result. For *A. niger*, it is cultured in a 30° C. incubator for 72 hours to observe the final results.

2.1.1.9.6 Evaluation Requirements (1) For product supervision and inspection, the test is repeated in triplicate according to the concentration and action time specified in the product instruction manual.

For each test of *Candida albicans* and *Aspergillus niger* having the logarithmic kill value of ≥4.00, if the logarithmic value of the test is ≥3.00, it can be determined that the product is qualified for disinfection of fungal pollutants.

(2) For hygiene license inspection for product declaration, test according to the use concentration and 3 action times specified in the product instruction manual and repeat the tests for three times, requiring the suspension quantitative killing test using the concentration and the shortest action time specified in the product instruction manual, and the minimum action time is 1.5 times, the logarithm value of each test should be ≥4.00, and when the concentration is 0.5 times of the minimum action time, the logarithm value of killing is allowed to be less than 4.00, then the product effective dose for disinfection of fungal contaminant tested in the laboratory can be determined.

For quantitative sterilization test using a carrier soaked with the product to evaluate the sterilization effect, the concentration and shortest action time according to the product specification is used, and when using 1.5 times of the shortest action time, the logarithm of the killing of each test is ≥3.00, and when using 0.5 times of the specified concentration and the shortest action time, the log value of killing is allowed to be less than 3.00, then the product effective dose for disinfection of fungal contaminant tested in the laboratory can be determined.

Example 3

Antiviral Efficacy Test

The antiviral efficacy of the example compositions are tested with identification test of physical removal method of residual disinfectant, according to sections 2.1.1.10.6 and 2.1.110.7 of Technical Standard for Disinfection (Ministry of Health of the People's Republic of China, 2002), which is incorporated herein by reference.

Identification test of physical removal method of residual disinfectant 2.1.1.10.6 operation procedures:

In the virus inactivation test, the physical removal method includes the dilution method, followed by the adsorption column method, molecular sieve column method, and carrier washing method.

(1) Grouping

1) Disinfectant+virus suspension→inoculate culture

Observe whether the tested disinfectant has an inactivation or inhibition effect on the virus, and whether it affects the normal growth of cells.

2) (Disinfectant+virus suspension)+drug removal treatment→inoculate culture

Observe whether the virus can restore the infection of cells after removing the residual drug.

3) Virus suspension+drug removal treatment→inoculate culture

Observe whether the drug removal treatment has any effect on virus titer.

4) Virus suspension→inoculation culture

Observe whether the virus growth is normal, and use this result as a positive control value.

5) Cells without inoculating with virus→Culture

Observe whether the cells are growing normally.

(2) Suspension Quantitative Operation Procedure

1) Group 1. 0.9 ml of detoxification agent to be tested is aspirated into a test tube, and placed in a water bath at 20° C.±1° C. for 5 minutes, then 0.1 ml of virus suspension is added and mixed well. After reacting for the required time for inactivation of the virus specified in the test, the final sample solution (or a serially diluted sample solution using an appropriate virus-innocuous dilution solution) is drawn according to the specified amount of the test, and the subsequent virus titer determination is performed.

2) Group 2. 0.9 ml of disinfectant to be tested is aspirated in the test tube, and placed in a 20° C.±1° C. water bath for 5 minutes, then 0.1 ml of the virus suspension is added and mixed well. After acting for a specified time, the solution is treated for drug-removal treatment, and the final sample (or serially diluted sample using appropriate virus-innocuous dilutions) is drawn according to the specified amount of the test for subsequent virus titer determination.

3) Group 3. 0.1 ml of virus suspension is aspirated and 0.9 ml of cell culture medium is added for drug removal treatment. According to the specified quantity in the test, the final sample (or serially diluted sample using appropriate virus-innocuous dilutions) is drawn, and then the subsequent virus titer determination is performed.

4) Group 4. 0.1 ml of virus suspension is pipetted, 0.9 ml of cell maintenance solution is added, without adding disinfectant or do any drug removal treatment. According to the specified amount of the test, the virus suspension (or serially diluted sample using appropriate virus-innocuous dilutions) is drawn, and then the subsequent virus titer determination is performed.

5) Group 5. For the non-virus-inoculated cell tube, complete cell culture medium was added for cultivation.

(3) Evaluation Requirements

If the test results meet all of the following conditions, the tested physical removal method can be judged as qualified:

1) Group 1 has no tested virus or only a small amount of growth.

2) Group 2 has much more tested virus growth than Group 1, but significantly less tested virus growth than Groups 3 to 5.

3) The third, fourth, and fifth (groups) tested virus growth is similar.

4) Obtain a passing evaluation for three consecutive tests.

5) Viral vectors can be used, and experiments are conducted according to the same principles and operating procedures, and the judgment criteria are the same.

Poliovirus inactivation test 2.1.1.10.7 operation procedures:

(1) Objective

To determine the dose of disinfectant required to inactivate Poliovirus (PV) to verify the effective dose of viral contaminants.

(2) Experimental Principle

The amount of poliomyelitis in the samples before and after treating the disinfectant (or experimental group and control group) was determined by the cell infection method. Cellular disease was used as a judgment index to determine the virus infection titer of each group, and to calculate the inactivation rate of disinfectant against poliomyelitis.

(3) Testing Groups

1) Test Group.

Based on the estimated disinfectant kill or inactivation dose to other microorganisms, an appropriate concentration and action time group (not less than 1 concentration, 3 action time) is set, and the design of the action time should not be less than 30 seconds.

2) Positive Control Group.

Deionized water is used instead of disinfectant, poliomyelitis suspension is added according to the prescribed steps of the test groups for testing and cultivation, and observe whether the poliomyelitis is growing well.

3) Negative Control Group.

A complete medium without poliomyelitis was used as a negative control to observe whether the medium used was contaminated and whether the cells were growing well.

(4) Procedure for Quantitative Inactivation Test of Polio Suspension

1) The frozen testing host cells are removed from liquid nitrogen, and quickly thawed at 37° C. in warm water, and washed twice with cell maintenance solution before transferring to a culture bottle with 10 ml complete medium. The cell growth day by day is observed and when the cells are overgrown with a single layer, they can be used for disinfection tests.

2) The cryopreserved poliomyelitis-1 strain is taken out, thawed in a 37° C. water bath, diluted with cell maintenance solution 10 times, and then inoculated in a cell bottle containing monolayer cells, and placed in a 37° C. incubator so that the virus can adsorb and grow with cells. The disease is observed day by day, and the virus is harvested when ¾ of the cells are damaged. When harvesting, the culture solution is removed, the host cells were disrupted by ultrasound or repeated freeze-thaw, centrifuged as soon as possible. 1.0 ml of the virus-containing supernatant were aliquoted into sterile centrifuge tubes (1.5 ml) per tube, and stored in a frozen place −80° C. for use.

3) The disinfectant to be tested is taken, diluted with sterilized hard water to 1.25 times the required concentration, and incubated in a water bath at 20° C.±1° C. for use.

4) 100 μl of organic interfering substances is mixed with 100 μl of virus stock solution, and the mixture is reacted in a water bath at 20° C.±1° C. for 5 minutes. 0.8 ml of disinfectant to be tested is add, and mixed immediately and the time is recorded. After the prescribed period of time, 0.1 ml of the mixture is taken out immediately and added to the neutralizing agent and mixed well; or treated with an approved drug removal method.

5) In the positive (virus) control group test, sterile deionized water is used instead of disinfectant to be tested.

6) The virus titer of each group is determined separately, which can be done by endpoint dilution method or plaque method.

7) The test is repeated 3 times.

8) End-point dilution method operation steps:

Firstly, cell maintenance culture solution is used to make a 10-fold serial dilution of the titrated sample. Then, the amount of virus remaining in each dilution sample is titrated on a 96-well culture plate, and 4 wells for each dilution are prepared (each of the wells should already be covered with a monolayer of host cells), and placed at 37° C. for 1 to 2 hours to ensure that all residual viruses are adsorbed on the cells. The culture plate is taken out and the cell maintenance medium is replaced. Continue to incubate in a carbon dioxide incubator (37° C., 5% CO2) for culturing. The cell lesions are observed under the microscope day by day for 3 days. The cell lesions were observed and recorded well by well. The calculation of virus infection titer by endpoint dilution method is expressed as half of cell infection dose (TCID50).

9) Operation Procedure of Plaque Method:

Firstly, cell maintenance culture solution is used to make a 10-fold serial dilution of the titrated sample, then inoculated in a cell culture flask, and the amount of virus remaining in the sample of each dilution is titrated. Before seeding the cells, the culture solution in the densely grown monolayer cells was decanted, 1 ml of the sample to be tested is added and placed at 37° C. to adsorb for 1-2 hours. The sample solution is decanted, and 3 ml of cell maintenance solution containing 0.8% agar is added. After cooling, the cell flask is flipped and incubated at 37° C. for 48-72 hours. Then, 2 ml of formaldehyde solution is added to each bottle of cells for fixing for a few minutes, rinsed with tap water and added crystal violet solution to stain for a few minutes, and subsequently rinsed and counted. The round and uncolored transparent area in the cell bottle is a plaque unit. The virus content in each milliliter of the test sample is calculated: pfu/ml=average number of plaques on the plate× dilution factor. Note: In order to facilitate counting, the number of virus plaques is generally Control between 10 pfu~30 pfu per cell flask.

(5) Calculation of Average Inactivation Logarithm

The average inactivation logarithm is calculated according to the following formula: set the average virus infection titer (TCID50 or pfu) of the positive (virus) control group as NO, and the average virus infection titer of the test (disinfection) group (TCID50 or pfu) is Nx. Average logarithmic inactivation value=log N0−log Nx (6) Evaluation Requirements 1) The poliovirus inactivation test can be used to evaluate the inactivation effect of chemical disinfectants for medical devices, tableware, surfaces and skins on viruses. The virus inactivation titer should reach 4 logarithms.

2) Under normal circumstances, the average log of inactivation of the three tests is ≥4.00, which can be determined as qualified for the laboratory test for disinfection of poliovirus pollutants. At the same time, the logarithm of the virus titer of the positive control group should be between 5 and 7.

(7) Precautions

1) The operator should have basic experience in virology experiments and try to use pipettes and sterile disposable tips.

2) In the sterilization test, a positive control should be set every time.

3) If the virus vector is used for testing, refer to the above suspension quantitative test procedure, and make appropriate modifications in accordance with the principles of virology before use.

Example 4

Antibacterial Activity of Chemical Disinfectants and Antiseptics under BS EN 1276:2009

Chemical disinfectants and antiseptics—Quantitative suspension test for the evaluation of bactericidal activity of chemical disinfectants and antiseptics used in food, industrial, domestic and institutional areas (phase 2, step 1)

Dilution recommended for use: No dilution

Product test concentration: 80% (w/w)

Experimental conditions

Contact time: 1 minute (for hand disinfection)

Test temperature: 20° C.

Appearance: Translucent viscous liquid

Interfering substance: 0.3 g/l bovine albumin (dirty condition)

Inhibition method: Dilution-neutralization

Neutralizing solution: D/E neutralizing broth—double strength (sodium thioglycollate 2.0 g/L, sodium thiosulfate 12.0 g/L, sodium bisulfite 5.0 g/L, Polysorbate 80 10.0 g/L, lecithin 14.0 g/L)

Incubation: 37° C., 48 hours

Agar medium: Trypticase Soy Agar

Test strains: *Escherichia coli* ATCC 10536, *Pseudomonas aeruginosa* ATCC 15442, *Staphylococcus aureus* ATCC 6538 and *Enterococcus* hirae ATCC 10541

Example 5

Durability Test

To evaluate the durability of bacteria inhibition of the exemplary compositions, durability test by regularly spiking a fixed amount of bacteria into the sample is performed and the procedures are incorporated herein by reference.

Preparation:

Group A: Agar plate with 0.5 mL distilled water;

Group B: Agar plate with 0.5 mL 75% isopropyl alcohol (IPA);

Group C: Agar plate with 0.5 g of tested exemplary composition.

Bacteria strain used: PolySeed® BOD Seed Inoculum Capsules (1 capsule dissolved into 500 mL Distilled Water) (Interlab), which contains a blend of broad spectrum bacteria designed specifically as a seed inoculum for the Biochemical Oxygen Demand (BOD 5) test as conducted in accordance to Standard Methods of the Examination of Water and Wastewater. PolySeed® is an EPA approved BOD 5 seed inoculum that has been used to seed both municipal and industrial wastes for almost 20 years.

Agar: Trypticase Soy Agar (TSA)

Incubation condition: 48 hours at 30±1° C.

Testing Procedure

The above three sample group agar plates are used as the sample matrices of different initial situation for spiking 0.5 ml bacteria solution for every 60 minutes, i.e.: there was an on-going process of spiking bacteria at time 0, 60, 120, 180, 240, 300 minutes;

A swab testing is carried out every 30 minutes from matrix samples of each group to test for the viable count of bacteria at the time interval.

Example of sample with sequence in time:

AM: 0.5 ml bacteria solution is added at $T_0$–10 min;

Sample A1: To swab from AM at $T_0$; Sample A2: To swab from AM at $T_1$;

AM: 0.5 ml bacteria solution is added at $T_2$–10 min;

Sample A3: To swab from AM at $T_2$; Sample A4: To swab from AM at $T_3$;

AM: 0.5 ml bacteria solution is added at $T_4$–10 min; and so forth. Table 2 summarized the testing schedule for durability test.

TABLE 1.2

Testing schedule for durability test.

Add 0.5 ml of bacteria solution to samples: AM, BM, CM; and waiting for 10 minutes

| Time (min) | A) Water Matrix | Samples | B) IPA Matrix | Samples | C) Sample composition Matrix | Samples |
|---|---|---|---|---|---|---|
| $T_0$ (0) | AM | A1 | BM | B1 | CM | C1 |
| $T_1$ (30) |  | A2 |  | B2 |  | C2 |
| $T_2$ (60) | AM | A3 | BM | B3 | CM | C3 |
| $T_3$(90) |  | A4 |  | B4 |  | C4 |
| $T_4$(120) | AM | A5 | BM | B5 | CM | C5 |
| $T_5$(150) |  | A6 |  | B6 |  | C6 |
| T6(180) | AM | A7 | BM | B7 | CM | C7 |
| $T_7$ (210) |  | A8 |  | B8 |  | C8 |
| $T_8$ (240) | AM | A9 | BM | B9 | CM | C9 |
| $T_9$ (270) |  | A10 |  | B10 |  | C10 |
| $T_{10}$ (300) | AM | A11 | BM | B11 | CM | C11 |

Example 6

Volatility Test

To study the duration on ability of bacteria inhibition of an exemplary composition, a volatility test is performed.

Preparation:

Group A: Agar plate with 0.5 mL distilled water;

Group B: Agar plate with 0.5 mL 75% isopropyl alcohol (IPA);

Group C: Agar plate with 0.5 g of tested exemplary composition.

Bacteria strain used: PolySeed® BOD Seed Inoculum Capsules (1 capsule dissolved into 500 mL Distilled Water) (Interlab)

Agar: Trypticase Soy Agar (TSA)

Incubation condition: 48 hours at 30±1° C.

Testing Procedure 0.5 mL bacteria solution is add into the agar plate groups A, B and C at the time interval of $T_x$. as defined in Table 1.3.

TABLE 1.3

Testing Schedule for volatility test

| Time (min) | A) Water Blank | Samples | B) IPA Blank | Samples | C) Example composition Blank | Samples |
|---|---|---|---|---|---|---|
| $T_0$ (0) | AB | A1 | BB | B1 | CB | C1 |
| $T_1$ (30) |  | A2 |  | B2 |  | C2 |
| $T_2$ (60) |  | A3 |  | B3 |  | C3 |
| $T_3$(90) |  | A4 |  | B4 |  | C4 |
| $T_4$(120) |  | A5 |  | B5 |  | C5 |
| $T_5$(150) |  | A6 |  | B6 |  | C6 |
| $T_6$(180) |  | A7 |  | B7 |  | C7 |
| $T_7$ (210) |  | A8 |  | B8 |  | C8 |
| $T_8$ (240) |  | A9 |  | B9 |  | C9 |
| $T_9$ (270) |  | A10 |  | B10 |  | C10 |
| $T_{10}$ (300) |  | A11 |  | B11 |  | C11 |
|  |  | Spike bacteria |  | Spike bacteria |  | Spike bacteria |

After $T_{10}$, bacteria solution is spiked to all the agar plates except agar blank.

Swab test is carried out to test for the viable count of bacteria at the time interval $T_x$.

Example 7

Efficacy of Bacterial Inhibition on Different Materials

To test for sanitization effectiveness on different materials, efficacy of bacterial inhibition of an exemplary composition on different materials is tested.

The exemplary composition to be tested is used to treat the surface of five different materials, including plastic, leather, glass, wood and ceramic tile. At each time interval Tx as shown in Table 1.4, bacterial solution is spiked on the surface of each testing material. The testing area to be examined is 5 cm×5 cm. After $T_2$ (i.e., 3 hours), the bacteria solution is spiked to each area that treated with the exemplary composition and waits for 10 minutes. A (positive) control is prepared with 0.5 ml bacteria solution to the agar plate without any treatment.

TABLE 1.4

Testing schedule for sanitization effectiveness

| Group | Materials | Time (Hour) | Sample composition |
|-------|-----------|-------------|--------------------|
| I | Plastic | $T_0$ ($_0$) | Ca1 |
| | | $T_1$ (1) | Ca2 |
| | | $T_2$ ($_3$) | Ca3 |
| II | Leather | $T_0$ ($_0$) | Cb1 |
| | | $T_1$ ($_1$) | Cb2 |
| | | $T_2$ ($_3$) | Cb3 |
| | Glass | $T_0$ ($_0$) | Cc1 |

TABLE 1.4-continued

Testing schedule for sanitization effectiveness

| Group | Materials | Time (Hour) | Sample composition |
|-------|-----------|-------------|--------------------|
| III | | $T_1$ ($_1$) | Cc2 |
| | | $T_2$ ($_3$) | Cc3 |
| | | $T_0$ ($_0$) | Cd1 |
| | | $T_1$ ($_1$) | Cd2 |
| | | $T_2$ ($_3$) | Cd3 |
| V | Ceramic Tile | $T_0$ ($_0$) | Ce1 |
| | | $T_1$ ($_1$) | Ce2 |
| | | $T_2$ ($_3$) | Ce3 |

Swab test is carried out to test for the viable count of the bacteria. The removal efficiency (%) is calculated by the following formula: Removal Efficiency (%)=(Viable count of Control–Viable count of Test)/Viable count of Control× 100%

Example 8

Toxicological Risk Assessment

The Toxicological Risk Assessment (TRA) is carried out according to general principle of toxicology and taking reference of EU and US cosmetic regulations and standards. The safety of the product for consumer health is reviewed. In certain exemplary embodiments, the product is intended for application on hands after hand wash for keeping it in good condition by children of one year old or above.

This review was compiled by using information gathered from raw material suppliers and various online databases including the EU Scientific Committee on Consumer Safety (SCCS) opinions, Cosmetic Ingredients Review (CIR); detailed references please refer to the SGS Scientific Archives.

Results

Example 9

Biocidal Efficacy Test Results

TABLE 2

Summarized Bactericidal and Fungicidal Efficacy Test Results. Negative control: No colony observed.

| Testing Microorganisms | Reaction concentration and time | Replicate | Positive control Colony count | Average Positive control Colony count (cfu/mL) | Log value of Positive control | Testing group colony count (cfu/mL) | Log value of Killing | Killing rate (%) |
|---|---|---|---|---|---|---|---|---|
| *Escherichia coli* 8099 | original conc., 5 minutes | 1 | $4.2 \times 10^7$ | $3.8 \times 10^7$ | 7.58 | <10 | ≥5.00 | >99.9999 |
| | | 2 | $3.9 \times 10^7$ | | | <10 | ≥5.00 | >99.9999 |
| | | 3 | $3.4 \times 10^7$ | | | <10 | ≥5.00 | >99.9999 |
| *Stapphylococcus aureus* ATCC 6538 | | 1 | $4.7 \times 10^7$ | $4.6 \times 10^7$ | 7.66 | <10 | ≥5.00 | >99.9999 |
| | | 2 | $4.8 \times 10^7$ | | | <10 | ≥5.00 | >99.9999 |
| | | 3 | $4.2 \times 107$ | | | <10 | ≥5.00 | >99.9999 |
| *Candida albicans* ATCC 10231 | | 1 | $3.2 \times 10^6$ | $2.8 \times 10^6$ | 6.45 | <10 | ≥5.50 | >99.999 |
| | | 2 | $2.8 \times 10^6$ | | | <10 | ≥5.45 | >99.999 |
| | | 3 | $2.4 \times 10^6$ | | | <10 | ≥5.38 | >99.999 |

Table 2 shows the summarized Biocidal Efficacy test results of composition A described in EXAMPLE 1 using the method described in EXAMPLE 2. Results show that within 5-minute reaction time, composition A surprisingly has a log value of killing of ≥5.00 and a killing rate of >99.999% for *E. coli, S. aureus* and *C. albicans*, respectively, indicating that the composition is effective in killing Gram negative and Gran positive bacteria and fungi such as yeasts with a short action time (within 5 minutes).

Example 10

Viral Efficacy Test Results

TABLE 3

Testing results of the Antiviral Efficacy Test for 30 seconds

| Testing virus and Host | Reacttion time and conc. | | Grouping | Virus titer of each group in each test ($lgTCID_{50}$/mL) | | |
| --- | --- | --- | --- | --- | --- | --- |
| | | | | Replicate 1 | Replicate 2 | Replicate 3 |
| Influenza A H3N2 and MDCK cells | Original conc. and 30 sec | 1st | Disinfectant + virus suspension | <1.50 | <1.50 | <1.50 |
| | | 2nd | (Disinfectant + virus suspension) + drug removal treatment | 2.50 | 2.43 | 2.50 |
| | | 3rd | Virus suspension + drug removal treatment | 5.90 | 6.00 | 6.00 |
| | | 4th | Virus suspension | 5.90 | 6.12 | 5.90 |
| | | 5th | Cells without inoculating with virus | | Good growth | |
| | | Experimental conclusion: The test result shows that the testing method is valid. | | | | |

TABLE 4

Testing results of the Antiviral Efficacy Test for 5 minutes

| Testing virus and Host | Reaction time and Conc. | Grouping | Virus titer of each group in each test ($lgTCID_{50}$/mL) | Average virus titer of each group in each test ($lgTCID_{50}$/mL) | Viral total count ($TCID_{50}$/ml) | Average Killing log value (KL) | Viral Killing rate (%) |
| --- | --- | --- | --- | --- | --- | --- | --- |
| Influenza A H3N2 and MDCK cells | Original conc. and 5 min | Control 1 | 5.90 | 5.90 | $8.08 \times 10^5$ | >4.40 | >99.99 |
| | | Control 2 | 5.80 | | | | |
| | | Control 3 | 6.00 | | | | |
| | | Testing 1 | <1.50 | <1.50 | <31.6 | | |
| | | Testing 2 | <1.50 | | | | |
| | | Testing 3 | <1.50 | | | | |

*The cells in the negative control group grew well, and the test results met all the conditions specified in the evaluation.

Tables 3 and 4 showing the summarized results of anti-viral efficacy of composition A described in EXAMPLE 1 using the method described in EXAMPLE 3. According to testing carried out under conditions specified in EXAMPLE 3, composition A surprisingly has a satisfactory anti-viral activity for Influenza A H3N2 for a reaction time of 30 seconds and 5 minutes, respectively, indicating that the composition is an effective anti-viral agent with a short action time (within 30 seconds).

Example 11

The results of Antibacterial Activity of composition B described in Example 1 under the method of BS EN 1276: 2009 in EXAMPLE 4 are shown in Tables 5-6.

TABLE 5

Control and validation results of an example composition tested under BS EN 1276:2009

| | Validation suspension ($N_y$) Criteria: $300 \le N_y \le$ | Method validation Criteria: $\ge 0.05 N_y$ | Validity |
| --- | --- | --- | --- |
| Test microorganism | 1600 | | |
| Escherichia coli (ATCC 10536) | 655 | 55 | valid |
| Pseudomonas aeruginosa (ATCC 15442) | 955 | 60 | valid |
| Staphylococcus aureus (ATCC 6538) | 645 | 58 | valid |
| Enterococcus hirae (ATCC 10541) | 750 | 62 | valid |

TABLE 6

Testing results of an example composition tested under BS EN 1276:2009

| Test microorganism | Initial suspension (N) No = (1/10N) Criteria: $1.5 \times 10^8 \le N \le 5 \times 10^8$ | Final count (Na) | R (Log$_{10}$Reduction) =Log No − Log Na Criteria: $R \ge 5.0$ | % Reduction Criteria: $R \ge 99.999$ | Assessment |
| --- | --- | --- | --- | --- | --- |
| Escherichia coli (ATCC 10536) | $3.2 \times 10^8$ | <140 | >5.3 | >99.999 | Satisfactory |

TABLE 6-continued

| | | | | | | |
|---|---|---|---|---|---|---|
| Testing results of an example composition tested under BS EN 1276:2009 | | | | | | |
| Test microorganism | Initial suspension (N) No = (1/10N) Criteria: $1.5 \times 10^8 \le N \le 5 \times 10^8$ | Final count (Na) | R (Log$_{10}$Reduction) =Log No – Log Na Criteria: R ≥ 5.0 | % Reduction Criteria: R ≥ 99.999 | Assessment | |
| *Pseudomonas aeruginosa* (ATCC 15442) | $4.6 \times 10^8$ | <140 | >5.5 | >99.999 | Satisfactory | |
| *Staphylococcus aureus* (ATCC 6538) | $2.8 \times 10^8$ | <140 | >5.3 | >99.999 | Satisfactory | |
| *Enterococcus hirae* (ATCC 10541) | $2.6 \times 10^8$ | <140 | >5.2 | >99.999 | Satisfactory | |

According to testing carried out under conditions specified in EN 1276, composition B surprisingly has a satisfactory bactericidal activity after 1 minute contact time at 20° C. under dirty conditions (0.3 g/L bovine serum albumin) for referenced strains *Escherichia coli* ATCC 10536, *Pseudomonas aeruginosa* ATCC 15442, *Staphylococcus aureus* ATCC 6538 and *Enterococcus* hirae ATCC 10541, indicating that the composition is effective in killing bacteria with a short contact time (within 1 minute).

Example 12

The results of Antibacterial Activity of composition C described in Example 1 under the method of BS EN 1276: 2009 in EXAMPLE 4 are shown in Tables 7-8.

TABLE 7

| | | | |
|---|---|---|---|
| Control and validation results of an example composition tested under BS EN 1276:2009 | | | |
| Test microorganism | Validation suspension (N$_v$) Criteria: 300 ≤ N$_v$ ≤ 1600 | Method validation Criteria: ≥ 0.05N$_v$ | Validity |
| *Escherichia coli* (ATCC 10536) | 1040 | 60 | valid |
| *Pseudomonas aeruginosa* (ATCC 15442) | 1575 | 108 | valid |
| *Staphylococcus aureus* (ATCC 6538) | 1310 | 94 | valid |
| *Enterococcus hirae* (ATCC 10541) | 1270 | 72 | valid |

TABLE 8

| | | | | | |
|---|---|---|---|---|---|
| Testing results of an example composition tested under BS EN 1276:2009 | | | | | |
| Test microorganism | Initial suspension (N) No = (1/10N) Criteria: $1.5 \times 10^8 \le N \le 5 \times 10^8$ | Final count (Na) | R (Log$_{10}$Reduction) =Log No – Log Na Criteria: R ≥ 5.0 | % Reduction Criteria: R ≥ 99.999 | Assessment |
| *Escherichia coli* (ATCC 10536) | $4.6 \times 10^8$ | <140 | >5.5 | >99.999 | Satisfactory |
| *Pseudomonas aeruginosa* (ATCC 15442) | $4.2 \times 10^8$ | <140 | >5.4 | >99.999 | Satisfactory |
| *Staphylococcus aureus* (ATCC 6538) | $4.2 \times 10^8$ | <140 | >5.4 | >99.999 | Satisfactory |
| *Enterococcus hirae* (ATCC 10541) | $4.6 \times 10^8$ | <140 | >5.5 | >99.999 | Satisfactory |

According to testing carried out under conditions specified in BS EN 1276, composition C surprisingly meets all of the criteria for bacterial activity ("satisfactory" score) after 1 minute contact time at 20° C. under dirty conditions (0.3 g/L bovine serum albumin) for referenced strains *Escherichia coli* ATCC 10536, *Pseudomonas aeruginosa* ATCC 15442, *Staphylococcus aureus* ATCC 6538 and *Enterococcus* hirae ATCC 10541, indicating that the composition is effective in killing bacteria with a short contact time (within 1 minute).

Example 13

Durability Test
Table 9 summarized the results of the durability test of exemplary composition B described in EXAMPLE 1 using the method described in EXAMPLE 5.

TABLE 9

| | | | | | Sample | |
|---|---|---|---|---|---|---|
| Time | Water | CFU/plate | 75% IPA | CFU/plate | composition | CFU/plate |
| $T_0$ (0 min) | A1 | 18 | B1 | 8 | C1 | 1 |
| $T_1$ (30 min) | A2 | 35 | B2 | 28 | C2 | 2 |
| $T_2$ (60 min) | A3 | 46 | B3 | 53 | C3 | 1 |
| $T_3$ (90 min) | A4 | 99 | B4 | 89 | C4 | 2 |
| $T_4$ (120 min) | A5 | 247 | B5 | 254 | C5 | 1 |
| $T_5$ (150 min) | A6 | 334 | B6 | 346 | C6 | 6 |
| $T_6$ (180 min) | A7 | Uncountable | B7 | Uncountable | C7 | 6 |
| $T_7$ (210 min) | A8 | Uncountable | B8 | Uncountable | C8 | 13 |
| $T_8$ (240 min) | A9 | Uncountable | B9 | Uncountable | C9 | 15 |
| $T_9$ (270 min) | A10 | Uncountable | B10 | Uncountable | C10 | 23 |
| $T_{10}$ (300 min) | A11 | Uncountable | B11 | Uncountable | C11 | 20 |

Results of durability test of an exemplary composition. "Uncountable" means the bacterial colonies are too numerous to be counted in the agar plate, e.g., more than 335 colonies per plate.

According to testing carried out under conditions specified in Example 5, composition B surprisingly has superior bactericidal activity over 75% IPA or water from treatment time 0 to 300 min, despite the fact that more bacteria was added at fixed time interval indicating that the exemplary composition provides good antimicrobial efficacy.

Example 14

Volatility Test

Table 10 summarized the results of durability test of exemplary composition B described in EXAMPLE 1 using method described in EXAMPLE 6.

TABLE 10

Summarized results of durability test

| Time | Water | CFU/plate | 75% IPA | CFU/plate | Sample composition | CFU/plate |
|---|---|---|---|---|---|---|
| $T_0$ (0 min) | A1 | 60 | B1 | 54 | C1 | 6 |
| $T_1$ (30 min) | A2 | 49 | B2 | 62 | C2 | 7 |
| $T_2$ (60 min) | A3 | 55 | B3 | 50 | C3 | 5 |
| $T_3$ (90 min) | A4 | 47 | B4 | 45 | C4 | 6 |
| $T_4$ (120 min) | A5 | 50 | B5 | 49 | C5 | 4 |
| $T_5$ (150 min) | A6 | 43 | B6 | 55 | C6 | 4 |
| $T_6$ (180 min) | A7 | 44 | B7 | 43 | C7 | 3 |
| $T_7$ (210 min) | A8 | 43 | B8 | 37 | C8 | 3 |
| $T_8$ (240 min) | A9 | 29 | B9 | 44 | C9 | 2 |
| $T_9$ (270 min) | A10 | 49 | B10 | 49 | C10 | 3 |
| $T_{10}$ (300 min) | A11 | 44 | B11 | 0 | C11 | 0 |

According to testing carried out under conditions specified in Example 6, composition B surprisingly maintains prolonged bactericidal activity over 75% IPA or water from treatment time 0 to 300 m.

Example 15

Efficacy of bacterial inhibition on different materials

Table 11 summarized the results of durability test of exemplary composition B described in EXAMPLE 1 using method described in EXAMPLE 7.

TABLE 11 summarized the results of durability test.

| Testing Material | Time (Hour) | Example composition CFU/plate | Bacterial Removal Efficacy (%) |
|---|---|---|---|
| Plastic | $T_0$ (0 Hour) | 0 | 100.0 |
| | $T_1$ (1 Hour) | 1 | 95.8 |
| | $T_2$ (3 Hour) | 0 | 100.0 |
| Leather | $T_0$ (0 Hour) | 2 | 91.7 |
| | $T_1$ (1 Hour) | 1 | 95.8 |
| | $T_2$ (3 Hour) | 1 | 95.8 |
| Glass | $T_0$ (0 Hour) | 1 | 95.8 |
| | $T_1$ (1 Hour) | 1 | 95.8 |
| | $T_2$ (3 Hour) | 0 | 100.0 |
| Wood | $T_0$ (0 Hour) | 4 | 83.3 |
| | $T_1$ (1 Hour) | 4 | 83.3 |
| | $T_2$ (3 Hour) | 1 | 95.8 |
| Ceramic Tile | $T_0$ (0 Hour) | 0 | 100.0 |
| | $T_1$ (1 Hour) | 1 | 95.8 |
| | $T_2$ (3 Hour) | 1 | 95.8 |
| Bacteria Solution (Control) | | 24 | |
| Summary | $T_0$ (0 Hour) | | 94.2 |
| | $T_1$ (1 Hour) | | 75.8 |
| | $T_2$ (3 Hour) | | 97.5 |
| | Overall | | 89.2 |

Notes:
Removal Efficacy (%) = (Control-Test) * 100/Control

According to testing carried out under conditions specified in Example 7, composition B has surprisingly effective bactericidal activity (80%-100% bacterial removal efficiency) on various material surfaces including plastic, leather, glass, wood and ceramic tile from treatment time from 0 to 3 hours indicating that the composition is an effective, long-lasting disinfectant to serve as surface coating for various materials.

Example 16

Toxicological Risk Assessment (TRA) Results
Consumer Health Risk Assessment

The exemplary formulation G in EXAMPLE 1 has been reviewed for safety by TRA described in EXAMPLE 8 at the basis of the following assumptions.

(1) Consumer Exposure Scenario
The following assumptions have been made for assessment of exposure:
Product category: Hand lotion
Physical form: Liquid Intended use (suggested use): Application on hands after hand wash for keeping them in good condition Frequency of use: 730 times per year (hand lotion) or 1825 times per year (after hand wash)

Exposure route(s): Primarily via dermal contact and inhalation of tiny amount of volatiles Amount per application: 1.7 g Exposure area: 302 cm$^2$ Exposure duration: 720 minutes or 192 minutes Body weight: 11.4 kg Target population: Children of one year old or above (2) Risk Characterization for Consumer Health (2.1) Local Effects Irritation: The product is not expected to cause skin and eye irritation under normal and reasonably foreseeable conditions of use. Accidental exposure of eyes may cause irritation, but the effect is expected to be minimal after rinsing.

Sensitization: There are no substances of known allergenic potentials and is not expected to produce sensitization in the majority of consumers.

Phototoxicity: Exposure to this product is unlikely to result in phototoxic effects.

(2.2) Systemic Effects

Provided the manufacturer's instructions are followed, all the ingredients used are of cosmetic or appropriate grade while the polymer is well-cured, this formulation is unlikely to cause damage to internal organs through skin under normal and reasonably foreseeable conditions of use. However, the product is intended for children of one year old or above who are more frequently associated with licking and sucking action. Although the formulation is not expected to be orally toxic when used as directed but just like ingestion of any non-food material, ingestion of significant amount of the product would cause discomfort and even harmful on repeated ingestion by intention or through hand-to-mouth transfer. It is recommended to change the intended users from children of one year to 3 years or above. It is also recommended to label the product to ensure its proper use. If there is an adverse reaction from using this formulation, then the undersigned should be informed so that the formulation can be further reviewed.

(2.3) Joint Toxic Action

Based on current knowledge, joint toxic action is not anticipated.

TRA Conclusions:

Provided the manufacturer's instructions are followed and all the ingredients used are of cosmetic or appropriate grade while the polymers are well-cured, it is considered that, in the present state of knowledge, the submitted formulation (composition G) put on the market is unlikely to pose a significant risk to the health of intended consumer under normal and reasonably foreseeable conditions of use. The product should be used by children of 3 years old or above. The product should be labelled to ensure its proper use and the following is suggested based on toxicological point of view.

Example 17

Formulations

Formulations for further exemplary compositions (proportion is in percentage (%) by weight) are described in Table 12.

TABLE 12

Further exemplary compositions in accordance with the present invention.

| | Composition | | |
|---|---|---|---|
| | H | I | J |
| Compound | | % by weight | |
| Glycerin | 13.0 | 11.9 | 13.0 |
| Caprylyl glycol | 2.9 | 2.8 | 2.9 |
| Ethoxydiglycol | 3.1 | 2.7 | 3.1 |
| Panthenol | 0.3 | 0.3 | 0.3 |
| Sodium polyacrylate | 0.2 | 0.2 | 0.3 |
| Phenoxyethanol | — | — | — |
| stearateEthylhexyl stearate | 0.11 | 0.11 | 0.15 |
| Trideceth-6 | 0.04 | 0.04 | 0.05 |
| Ethylhexylglycerin | 0.9 | 0.9 | 0.9 |
| Carbomer | — | — | — |
| 1,2-Hexanediol | 1.5 | 1.5 | 1.5 |
| Sodium Dodecylbenzenesulfonate | — | — | — |
| Sodium Citrate | — | — | — |
| Silver Sulfate | — | — | — |
| Silver | — | — | — |
| Benzyl alcohol | — | — | — |
| Avena sativa (Oat) Kernel Flour | — | — | 1 |
| water | Up to 100 | Up to 100 | Up to 100 |

In certain exemplary embodiments, the composition contains glycerin, caprylyl glycol and a first ingredient, wherein the first ingredient is ethoxydiglycol. Glycerin, caprylyl glycol and the first ingredient together form a first component. In certain exemplary embodiments, the first component consists essentially of glycerin, caprylyl glycol and ethoxydiglycol. In other embodiments, the first component contains glycerin, caprylyl glycol, and ethoxydiglycol, the sum of which is about 13%, 14%, 15%, 16%, 17%, 18%, 19%, 20%, or 21% by weight, in other embodiments, 17.4%, or 19.0% by weight. In a further exemplary embodiment, the first component contains about 8.5%-16% glycerin, about 0.45-3% caprylyl glycol and 1-5% ethoxydiglycol, and the first component is more than about 13% by weight, as shown in Table 12.

In certain exemplary embodiments and as seen in Composition H above, the composition may essentially contain about 13.0% of the glycerin, about 2.9% caprylyl glycol, and about 3.1% ethoxydiglycol and water up to 100%. In these embodiments, the composition does not essentially contain acrylates/C10-30. The composition may further contain about 0.3% panthenol by weight, about 0.2% sodium polyacrylate by weight, about 0.11% ethylhexyl stearate by weight, about 0.04% trideceth-6 by weight, about 0.9% ethylhexylglycerin by weight, and about 1.5% 1,2-hexanediol by weight. In this exemplary embodiment, the composition does not essentially contain phenoxyethanol, carbomer, sodium dodecylbenzenesulfonate, sodium citrate, silver sulfate, silver, nor benzyl alcohol.

In certain exemplary embodiments and as seen in Composition I above, the composition may essentially contain about 11.9% of glycerin, about 2.8% caprylyl glycol and about 2.7% ethoxydiglycol and water up to 100%. The composition may further contain about 0.3% panthenol by weight, about 0.2% sodium polyacrylate by weight, about 0.11% ethylhexyl stearate by weight, about 0.04% Trideceth-6 by weight, about 0.9% ethylhexylglycerin by weight, and about 1.5% 1,2-hexanediol by weight. In this exemplary embodiment, the composition does not essentially contain phenoxyethanol, carbomer, sodium dodecylbenzenesulfonate, sodium citrate, silver sulfate, silver, nor benzyl alcohol.

In certain exemplary embodiments and as seen in Composition J above, the composition may essentially contain about 13.0% glycerin, about 2.9% caprylyl glycol, and about 3.1% ethoxydiglycol and water up to 100%. The composition may further contain about 0.3% panthenol by weight, about 0.3% sodium polyacrylate by weight, about 0.15% ethylhexyl stearate by weight, about 0.05% Trideceth-6 by weight, about 0.9% ethylhexylglycerin by weight, and about 1.5% 1,2-hexanediol by weight. In a further exemplary embodiment and as seen in Composition J, the composition may further contain about 1% *Avena sativa* (Oat) Kernel Flour by weight. In this exemplary embodiment, the composition does not essentially contain phenoxyethanol, carbomer, sodium dodecylbenzenesulfonate, sodium citrate, silver sulfate, silver, nor benzyl alcohol.

Methods of making the exemplary Formulations (Compositions H, I and J) are similar to the methods as described in Example 1.

Example 18

Virucidal efficacy against human coronavirus Strain 229E

Standard Test Method to Assess the Activity of Microbicides Against Viruses in Suspension (ASTM E0152)

Test Microorganism: Human coronavirus, Strain 229E, ATCC VR-740

Host Cell: MRC-5 (ATCC CCL-171)

Test Substance: Composition H

Test Substance Active Ingredients: Glycerin, caprylyl glycol and ethoxydiglycol

Test Substance Dilution: No Dilution. Ready to use liquid test substance

Total Organic Soil Load: No supplementation of organic soil load incorporated into the test inoculum Number of Replicates Per Lot: Triple Contact Time: 1 minute Exposure Temperature: Room temperature (20.8-21.0° C.) and 45-46% Relative Humidity (RH)

Neutralization Method: Dilution method using fetal bovine serum (FBS)

Test Procedure

Stock virus was thawed and was not supplemented with an organic soil load;

Test and virus control substances were dispensed in 9-part equivalent volumes into sterile vessels;

The test suspensions were held for the contact time as stated above, and then neutralized by ten-fold serial dilutions into the appropriate solution;

The virus control suspensions were neutralized in the same manner as the test suspension; Following neutralization, the viral suspensions were quantified to determine the levels of infectious virus using standard cell culture (e.g. $TCID_{50}$) assay techniques;

The cell culture plates were incubated for the period most suitable for the virus-host cell system (e.g. around 7 days);

After the incubation period, the assay was scored for the presence/absence of test virus and cytotoxic effects. The appropriate calculations were performed (e.g. Spearman-Karber) to determine viral titers and levels of test substance cytotoxicity, where applicable;

$Log_{10}$ and percent reductions were computed for test suspensions relative to the control suspensions;

Unless otherwise noted, no modifications to the method were made for this study.

Success Criteria

The following measures are met to ensure the acceptability of virucidal efficacy data:

The virus titer control demonstrate obvious and or typical cytopathic effects on the monolayers unless a detection method other than cytopathic effect is used;

Neutralization of the test substance with a low titer (e.g. 1000-5000 infective units) of the test virus is demonstrated;

Quantification of the test and control parameters are conducted at a minimum of four determinations per dilution.

The Product Performance Criteria Follows:

The log and percent reduction of the test virus following exposure to the test substance are calculated however, there is no minimum reduction level to qualify as "passing" or an "efficacious" product.

Calculations and Statistics Analysis

The $TCID_{50}$ (Tissue Culture Infectivity Dose) represents the endpoint dilution where 50% of the cell cultures exhibit cytopathic effects due to infection by the test virus. The endpoint dilution at which 50% of the host cell monolayers exhibit cytotoxicity is termed the Tissue Culture Dose ($TCD_{50}$) The $TCID_{50}$, and $TCD_{50}$ was determined using the Spearman-Karber method and calculated as follows:

$$\text{Negative logarithm of endpoint titer} = [-\text{Log of first dilution inoculated}] - [((\text{sum of \% mortality at each dilution}/100) - 0.5) \times \text{Logarithm of dilution}]$$

The result of this calculation is expressed as $TCID_{50}/0.1$ ml (or volume of dilution inoculated) for the test, virus control, and neutralization control and $TCD_{50}/0.1$ ml (or volume of dilution inoculated) for the cytotoxicity control.

Calculation of the Log Reduction

The log reduction in viral titer was calculated as follows:

$$\text{Plate Recovery Control Log}_{10} \text{ TCID}_{50} - \text{Virus-Test Substance Log}_{10} \text{ TCID}_{50}$$

Calculation of the Percent Reduction

The percent reduction in viral titer was calculated as follows:

$$\text{Percent Reduction} = 1 - (C/B) \times 100, \text{ where:}$$

B=Average $TCID_{50}$ of virus in control suspensions.

C=Average $TCID_{50}$ of virus in virus-test suspensions.

The presence of any test substance cytotoxicity was taken into account when calculating the log and percent reductions in viral titer.

If multiple virus control and test replicates were performed, the average $TCID_{50}$ of each parameter was calculated and the average result was used to calculate the log reductions in viral titer.

Example 19

Test Results of Virucidal Efficacy Against Human Coronavirus Strain 229E

The test results of virucidal efficacy of exemplary Compositions containing first component #2 (Glycerin/Caprylyl glycol/Ethoxydiglycol) using Methods of Standard Test Method to Assess the Activity of Microbicides Against Viruses in Suspension described in EXAMPLE 18 are shown in Tables 13-16.

The purpose of the test was to determine the virucidal efficacy of Composition B against Human coronavirus Strain 229E, with no supplementation of organic soil load incorporated into the test inoculum, at contact times of 1 minute, at room temperature (20.8-21.0° C. and 45-46% RH).

TABLE 13

| | | Virus Titer | Virus Control Replicate #1 | Virus Control Replicate #2 | Virus Control Replicate #3 |
|---|---|---|---|---|---|
| Virus Titer and Virus Controls. | | | | | |
| Cell Control | | 0 0 0 0 | 0 0 0 0 | 0 0 0 0 | 0 0 0 0 |
| Dilution | $10^{-1}$ | N/A | N/A | N/A | N/A |
| | $10^{-2}$ | + + + + | + + + + | + + + + | + + + + |
| | $10^{-3}$ | + + + + | + + + + | + + + + | + + + + |
| | $10^{-4}$ | + + + + | + + + + | + + + + | + + + + |
| | $10^{-5}$ | + + + + | + + + + | + + + + | + + + + |
| | $10^{-6}$ | + + + + | + 0 0 0 | + 0 + + | + 0 0 + |
| | $10^{-7}$ | 0 0 0 + | 0 0 0 0 | 0 0 0 0 | 0 0 0 0 |
| $TCID_{50}$ per 0.1 ml | | 6.75 $Log_{10}$ | 5.75 $Log_{10}$ | 6.25 $Log_{10}$ | 6.00 $Log_{10}$ |
| Average $TCID_{50}$ per 0.1 ml | | N/A | 6.05 $Log_{10}$ | | |

Key:
"+" = Virus recovered;
"0" = Virus not recovered and/or no cytotoxicity observed;
"T" = Cytotoxicity observed;
"N/A" = not applicable

TABLE 14

| | | Cytotoxicity Control |
|---|---|---|
| Cytotoxicity Control Results. | | |
| Cell Control | | 0 0 0 0 |
| Dilution | $10^{-1}$ | N/A |
| | $10^{-2}$ | T T T T |
| | $10^{-3}$ | 0 0 0 0 |
| | $10^{-4}$ | 0 0 0 0 |
| $TCD_{50}$ per 0.1 ml | | 2.50 $Log_{10}$ |

Key:
"+" = Virus recovered;
"0" = Virus not recovered and/or no cytotoxicity observed;
"T" = Cytotoxicity observed;
"N/A" = not applicable

TABLE 15

| | | Neutralization Control |
|---|---|---|
| Test Substance Neutralization Control Results. | | |
| Cell Control | | 0 0 0 0 |
| Dilution | $10^{-1}$ | N/A |
| | $10^{-2}$ | T T T T |
| | $10^{-3}$ | + + + + |
| | $10^{-4}$ | + + + + |
| Neutralized at $TCD_{50}$ per 0.1 ml | | 2.50 $Log_{10}$ |

Key: "+" = Virus recovered;
"0" = Virus not recovered and/or no cytotoxicity observed;
"T" = Cytotoxicity observed;
"N/A" = not applicable

TABLE 16

| | | Test Results Replicate #1 | Test Results Replicate #2 | Test Results Replicate #3 |
|---|---|---|---|---|
| Composition H at a contact time of 1 minute. | | | | |
| Cell Control | | 0 0 0 0 | 0 0 0 0 | 0 0 0 0 |
| Dilution | $10^{-1}$ | N/A | N/A | N/A |
| | $10^{-2}$ | T T T T | T T T T | T T T T |
| | $10^{-3}$ | 0 0 0 0 | 0 0 0 0 | 0 0 0 0 |
| | $10^{-4}$ | 0 0 0 0 | 0 0 0 0 | 0 0 0 0 |
| | $10^{-5}$ | 0 0 0 0 | 0 0 0 0 | 0 0 0 0 |
| | $10^{-6}$ | 0 0 0 0 | 0 0 0 0 | 0 0 0 0 |
| | $10^{-7}$ | 0 0 0 0 | 0 0 0 0 | 0 0 0 0 |

TABLE 16-continued

| | | Test Results Replicate #1 | Test Results Replicate #2 | Test Results Replicate #3 |
|---|---|---|---|---|
| Composition H at a contact time of 1 minute. | | | | |
| $TCID_{50}$ per 0.1 ml | | ≤2.50 $Log_{10}$ | ≤2.50 $Log_{10}$ | ≤2.50 $Log_{10}$ |
| Average $TCID_{50}$ per 0.1 ml | | ≤2.50 $Log_{10}$ | | |
| Average Log Reduction | | ≥3.55 $Log_{10}$ | | |
| Average Percent Reduction | | ≥99.97% | | |

Key: "+" = Virus recovered;
"0" = Virus not recovered and/or no cytotoxicity observed;
"T" = Cytotoxicity observed;
"N/A" = not applicable Table 13 shows that the Virus Titer is 6.75 $Log_{10}$ $TCID_{50}$ per 0.1 ml of while the Virus Control demonstrated an average viral titer of 6.05 $Log_{10}$ $TCID_{50}$ per 0.1 ml.

Table 14 shows that the Tissue Culture Dose for the Cytotoxicity Control was 2.50 $Log_{10}$ $TCD_{50}$ per 0.1 ml.

Table 15 shows that the Test Substance Neutralization Control demonstrated that the test substance was neutralized at 2.50 $Log_{10}$ for the lot assayed.

Table 16 shows that, taking the cytotoxicity test results in Table 14 and the neutralization control results in Table 15 into consideration, the evaluated test substance, exemplary Composition H, demonstrated an average of ≥3.55 $Log_{10}$ reduction (≥99.97%) in viral titer at a contact time of 1 minute.

According to testing carried out under conditions specified in Example 18, exemplary composition H surprisingly has superior virucidal activity at a contact time of 1 minute, indicating that the exemplary compositions provide good antiviral efficacy.

Example 20

Virucidal Efficacy Against Corona Virus Disease 2019 (COVID-19)

Methodology 0.1 mL of media containing $1 \times 10^4$ SARS-CoV-2 (COVID-19) virus was mixed with 0.1 mL of the exemplary Composition H and incubated for 5 minutes. The treated viruses were exposed to human renal cells (~80% confluency) plated on a 12-well plate for 30 minutes at 37° C. supplemented with 5% carbon dioxide ($CO_2$). Three serial dilutions were prepared. Infected cells were covered with 0.5 mL of a sterile solution containing 2% carboxymethyl cellulose and MEM (×2) supplemented with fetal calf serum (10%), pyruvic acid, and non-essential amino acids. The plates were incubated at 37° C. supplemented with 5% $CO_2$ for 48 hours. Then, the plates were washed with PBS to remove the carboxymethyl cellulose solution, and 4% p-formaldehyde was used as a fixative for 30 minutes. Crystal violet (1%) was added to the wells for 15 min and washed until plaques were observed. Infected and non-infected cells were used as positive and negative controls, respectively.

Results

Positive control showed plaques formation while negative control showed no plaque formation. Test results showed no plaques formation at the indicated time (i.e., treated for 5 minutes), indicating a complete inactivation of the SARS-CoV-2 virus.

Conclusion

According to testing carried out under conditions specified in this Example 20, exemplary Composition H surprisingly has superior inactivation activity to SARS-CoV-2 (COVID-19) viruses at a contact time of 5 minutes, indicating that the exemplary compositions provide good antiviral efficacy.

Example 21

Tests for Treatment of Dermatitis

Three patients with dermatitis who did not respond well to typical topical agents were enrolled for test.

Case 1

Patient 1: a 12-year old Asian teenager. Overall healthy with no history of any health issues except atopic dermatitis.

Symptoms prior to treatment: Because of the genetic predisposition and immune system dysfunction, the patient's skin often develops moderately severe dryness, thickening, and skin cracks. Patient 1 would feel stiffening in his skin even when the skin was not inflamed. During active inflammation, Patient 1 would experience tearing pain and itchiness that would often respond only to potent topical steroids such as Betamethasone Dipropionate or Mometasone in ointment. The ointment base gave the patient some relief but it also came with a stickiness on the skin that was unpleasant especially during hotter weather.

Figure 1A:
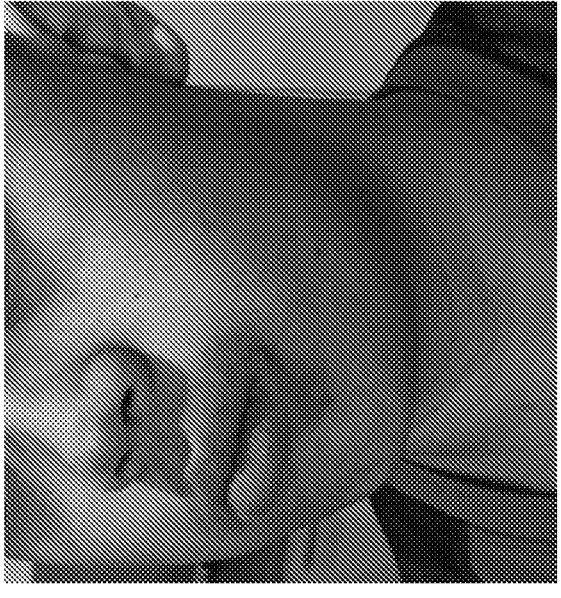
FIG. 1A is a picture showing Patient 1's face before use of exemplary Composition, according to an example embodiment.

Treatment: FIG. 1A shows the patient's typical skin condition even after prolonged use of existing topical steroids (prior to treatment of the exemplary composition). Dryness, skin thickening, flakiness and skin cracks were still visible especially around the patient's mouth. Patient 1 was introduced to the Composition H, with a small amount (less than a 50 cent coin size) applying only around mouth area. The Composition H was applied around 3 times a day for two days.

Results: After two days of application, his skin inflammation began to calm down. There was clear improvement in the skin texture and thickening. Skin flakiness and crack reduced significantly. After a week of Composition H application without the use of any other prescription topical agent, his skin improved dramatically, as shown in FIG. 1B. The patient also reported less skin stiffness. An additional benefit is an increase in his self-esteem and confidence due to the patient's much-improved facial appearance.

Case 2

Patient 2: a young lady around 30 years old. She works as a Project Manager for a commercial building construction company. Her job has been challenging. She is required to visit different construction sites.

Figure 2B:
FIGS. 2A and 2B are pictures showing Patient 2's left palm and right palm, respectively, before use of exemplary Composition, according to an example embodiment.
Figure 2A:
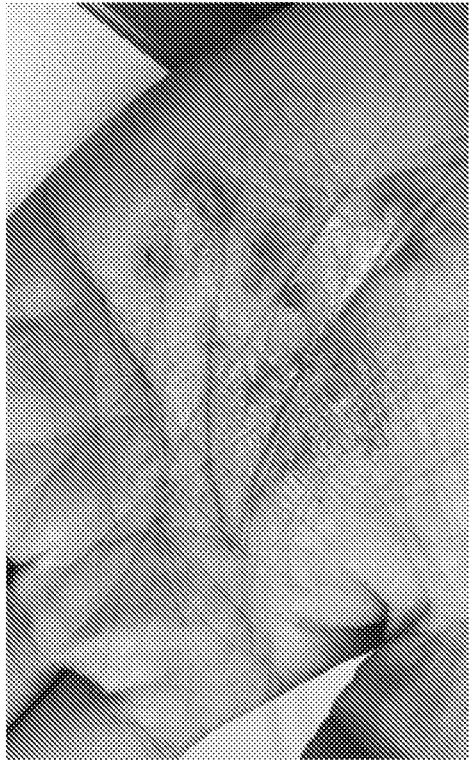

Symptoms prior to treatment: She has no known medical issues, and no drug or environmental allergy. Because of the pandemic and meetings with different people, the patient had been very diligent with maintaining hand hygiene by frequently using alcohol-based hand sanitizers throughout the day. After a short time, the patient's hands developed significant dryness, skin thickening, erythema and itch. Patient 2 initially thought that it was just dryness from frequent washing. The patient's condition became worse. Patient 2 noticed some tiny blisters forming along the side of her right-hand fingers. The blisters slowly spread to her right palms and developed intense itch which even woke her up from sleep. After a visit to her doctor, the patient was diagnosed with dyshidrotic eczema. Patient 2 has been prescribed a potent topical corticosteroid cream. Unfortunately, after one week of corticosteroid treatment, there was minimal improvement only. The patient's right palm turned red. Patient 2 also noticed more tiny blisters forming in her left palm as well. FIGS. 2A-2B show her hand conditions after the mentioned corticosteroid treatment (prior to treatment of the exemplary composition H). Because of the intense itch, the eczematous blisters were mostly excoriated. Patient 2 reported that those tiny craters felt like active volcanos causing significant burning sensation when Patient 2 used alcohol-based sanitizers.

Treatment: As the patient's condition became worse, Patient 2 was introduced to Composition B as an alternative treatment. Composition H was applied to the hands of Patient 2 (around size of a one dollar coin) for around three times a day for 2 weeks.

Figure 2D:
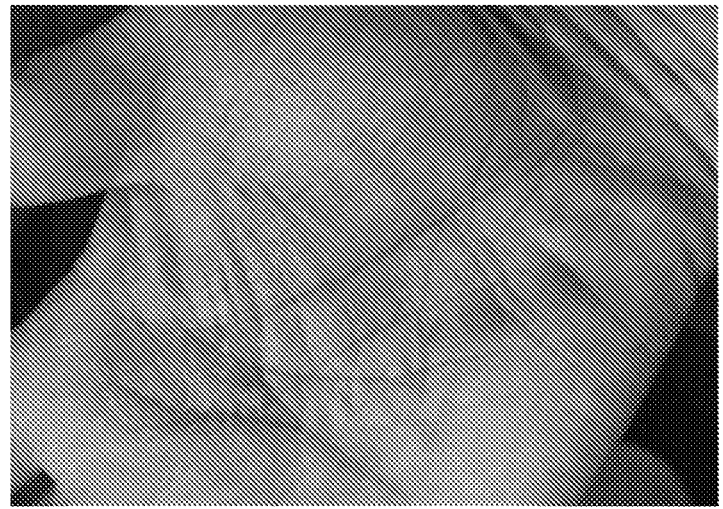
FIGS. 2C and 2D are pictures showing the same patient's left palm and right palm, respectively, after use of exemplary Composition, according to the same example embodiment of FIGS. 2A and 2B.
Figure 2C:

Results: Significant improvements were observed after the treatment. First, Patient 2 did not experience any burning sensation when using the Composition H as a hand sanitizer. Second, after one week, the tiny blisters reduced by half and her skin dryness also resolved. Third, after a few more weeks, her dyshidrotic eczema completely resolved with no more blisters, itch, or skin dryness. FIGS. 2C-2D show her hand conditions after treatment with the use of Composition H.

Case 3

Patient 3: a 60-year old Asian car salesman.

Figure 3B:
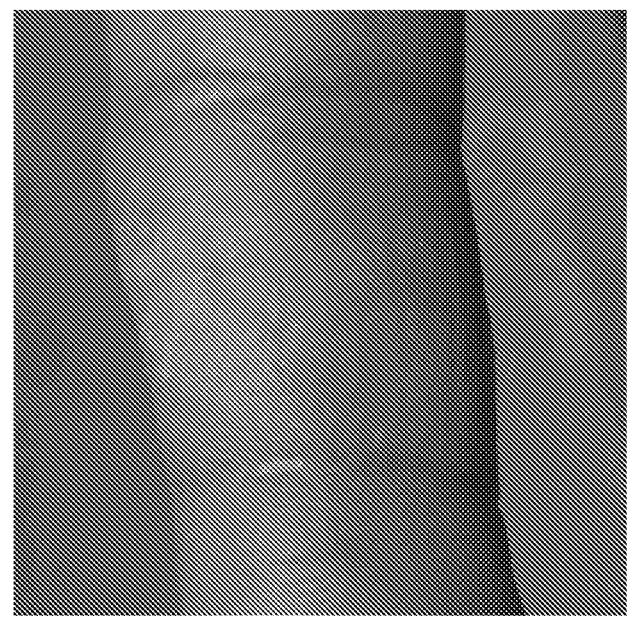
FIG. 3B is a picture showing the same patient's finger after use of Composition B, according to the same example embodiment of FIG. 3A.
Figure 3A:
FIG. 3A is a picture showing the Patient 3's finger before use of Composition B, according to an example embodiment.

Symptoms prior to treatment: Patient 3 has a history of hypertension dyslipidemia, and premature ventricular complex. Patient 3 has no history diabetes, seasonal allergy, or congenital skin disease. The patient's current medication includes only Diltiazem and Rosuvastatin. Because of the patient's job nature, Patient 3 requires frequent use of car cleaning products and is exposed to increased levels of allergens such as volatile organic compounds. For over a decade, Patient 3 has been suffering from irritant contact dermatitis. One of the patient's worst episodes is when Patient 3 had a major flare-up of skin inflammation after frequent use of alcohol-based hand sanitizers during the COVID-19 pandemic. Patient 3 has been prescribed different steroid-based compounds. Patient 3 was even prescribed the non-steroid immune modulators. Unfortunately, Patient 3 still continued to experience painful skin cracks, skin thinning, and burning sensation. FIG. 3A shows the picture of the patient's finger in its best condition after use of potent steroid ointment (prior to treatment of the exemplary Composition H).

Treatment: Composition H was introduced to the patient as a regular skin cream with a small amount (less than a 50 cent coin size) applying only to fingers around three times a day for 1 day.

Results: After a day of regular application without use of any prescription topical medication, the patient's finger skin condition improved further as shown in FIG. 3B.

CONCLUSION

Exemplary Composition H, which is a non-alcohol and non-steroid formulation having antimicrobial properties, showed significant improvements on skin conditions to the above-mentioned 3 Patients in all cases who suffer from different conditions of dermatitis and did not respond well to typical topical agents, indicating that the exemplary compositions not only are useful as skin sanitizers, but also useful as topical agents for skin, especially treating or improving conditions of dermatitis, dryness and/or allergic reactions to alcohol-based sanitizers.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

What is claimed is:

1. An aqueous antiseptic composition consisting of:
a) glycerin about 8.5-16% by weight;
b) caprylyl glycol about 2-3% by weight;
c) ethoxydiglycol about 1-5% by weight;
d) panthenol about 0.1 to 1%; and
e) sodium polyacrylate about 0.1 to about 0.5%, and
f) one or more compounds selected from the group consisting of
phenoxyethanol about 0-1% by weight,
ethylhexyl stearate about 0-1% by weight,
Trideceth-6 about 0-1% by weight,
ethylhexylglycerin about 0-2% by weight,
1,2-hexanediol about 0-5% by weight,
acrylates/C10-30 alkyl acrylate crosspolymer about 0-0.1% by weight,
carbomer about 0-1% by weight,
sodium dodecylbenzenesulfonate about 0-0.005% by weight,
sodium citrate about 0-0.0006% by weight,
silver sulfate about 0-0.00015% by weight,
silver about 0-0.00015% by weight,
benzyl alcohol about 0-1% by weight, and
*Avena sativa* (Oat) Kernel Flour 0% or about 1% by weight;
g) water up to 100% by weight;

wherein the glycerin, the caprylyl glycol and the ethoxydiglycol taken together is more than about 13% by weight and less than 25% by weight of the antiseptic composition.

2. The aqueous antiseptic composition of claim 1, wherein the composition is free of ethylhexyglycerin.

3. The aqueous antiseptic composition of claim 1, wherein the composition is free of phenoxyethanol.

4. The aqueous antiseptic composition of claim 1, wherein the acrylates/C10-30 alkyl acrylate crosspolymer is about 0.01-0.1% by weight of the antiseptic composition.

5. The aqueous antiseptic composition of claim 1, wherein the carbomer is about 0.1-1% by weight of the antiseptic composition.

6. The aqueous antiseptic composition of claim 1, wherein the 1, 2-hexanediol is about 1-5% by weight of the antiseptic composition.

7. The aqueous antiseptic composition of claim 1, wherein the composition is capable of exhibiting greater than a 4 log 10 kill of a microorganism within 5 minutes.

8. The aqueous antiseptic composition of claim 7, wherein the microorganism is a bacterium, a fungus, a yeast, a mold, a virus or a combination thereof.

9. The aqueous antiseptic composition of claim 8, wherein the virus is H3N2 influenza A virus.

10. The aqueous antiseptic composition of claim 8, wherein the virus is a human coronavirus.

11. The aqueous antiseptic composition of claim 10, wherein the human coronavirus is strain 229 E or COVID-19.

12. The aqueous antiseptic composition of claim 8, wherein the microorganism is one or more of *Escherichia coli, Staphylococcus aureus, Candida albicans*, H3N2 influenza A virus and human coronavirus.

13. A method of alleviating or treating at least one skin condition in a subject in need thereof, comprising:
administering a therapeutically or prophylactically effective amount of the composition of claim 1 to the subject to treat the at least one skin condition, and wherein the at least one skin condition is dermatitis or is selected from a group consisting of eczematous blisters, skin dryness, skin thickening, skin thinning, skin cracks, skin flakiness, skin inflammation, itchy skin, dyshidrotic eczema, irritant contact dermatitis, skin allergies to alcohol, skin stiffness, atopic dermatitis, and erythema.

14. The method of claim 13, wherein the composition is administered topically.

\* \* \* \* \*